(12) United States Patent
Darekar et al.

(10) Patent No.: US 12,171,678 B2
(45) Date of Patent: Dec. 24, 2024

(54) SKIRT-REINFORCEMENT MEMBERS FOR PROSTHETIC VALVE DEVICES

(71) Applicant: Medtronic, Inc., Minneapolis, MN (US)

(72) Inventors: Yogesh Darekar, Irvine, CA (US); Brenda McIntire, Walnut Creek, CA (US); Eric Pierce, Mission Viejo, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 260 days.

(21) Appl. No.: 17/591,028

(22) Filed: Feb. 2, 2022

(65) Prior Publication Data

US 2022/0265450 A1  Aug. 25, 2022

Related U.S. Application Data

(60) Provisional application No. 63/152,982, filed on Feb. 24, 2021.

(51) Int. Cl.
*A61F 2/95* (2013.01)
*A61F 2/24* (2006.01)

(52) U.S. Cl.
CPC .............. *A61F 2/95* (2013.01); *A61F 2/2409* (2013.01); *A61F 2/2418* (2013.01); *A61F 2/2427* (2013.01); *A61F 2002/9511* (2013.01)

(58) Field of Classification Search
CPC ........ A61F 2/95; A61F 2/2418; A61F 2/2427; A61F 2002/9511; A61F 2/2409
See application file for complete search history.

(56) References Cited

U.S. PATENT DOCUMENTS

| | | | |
|---|---|---|---|
| 6,805,706 B2 | 10/2004 | Solovay et al. | |
| 7,993,394 B2 | 8/2011 | Hariton et al. | |
| 9,681,951 B2 | 6/2017 | Ratz et al. | |
| 10,195,025 B2 | 2/2019 | Levi et al. | |
| 10,441,416 B2 | 10/2019 | Oba et al. | |
| 2008/0033543 A1 | 2/2008 | Gurskis et al. | |
| 2018/0256377 A1 | 9/2018 | Shalev | |
| 2018/0263765 A1 | 9/2018 | Flaction | |
| 2018/0333259 A1* | 11/2018 | Dibie | A61F 2/2418 |
| 2019/0175338 A1* | 6/2019 | White | A61F 2/2409 |
| 2019/0231514 A1 | 8/2019 | Arbefeuille | |

(Continued)

FOREIGN PATENT DOCUMENTS

| | | |
|---|---|---|
| CA | 3109254 A1 | 8/2020 |
| WO | 2019/086958 A1 | 5/2019 |

OTHER PUBLICATIONS

European Search Report issued Jul. 25, 2022 in European Patent Appl. No. 22157500.4.

*Primary Examiner* — Paul B Prebilic
(74) *Attorney, Agent, or Firm* — MEDLER FERRO WOODHOUSE & MILLS PLLC

(57) ABSTRACT

A skirt-reinforcement member for supporting or reinforcing an unsupported portion of a skirt that spans across a side opening of a stent or frame of a valve prosthesis. The skirt-reinforcement member is configured to prevent billowing of the skirt material that spans across the side opening of the inner frame of the valve prosthesis, as such billowing may undesirably result in contact between the skirt and leaflets of the valve prosthesis after the valve prosthesis is deployed in situ.

20 Claims, 18 Drawing Sheets

(56) References Cited

U.S. PATENT DOCUMENTS

| | | |
|---|---|---|
| 2019/0262129 A1 | 8/2019 | Cooper et al. |
| 2019/0321171 A1* | 10/2019 | Morriss ................ A61F 2/2436 |
| 2020/0330222 A1* | 10/2020 | Miyashiro ............. A61F 2/2418 |
| 2020/0352670 A1* | 11/2020 | Aguila ................. A61F 2/2415 |

* cited by examiner

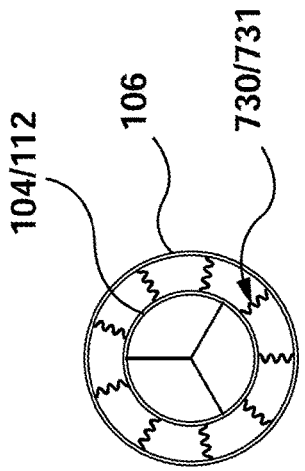
FIG. 8B
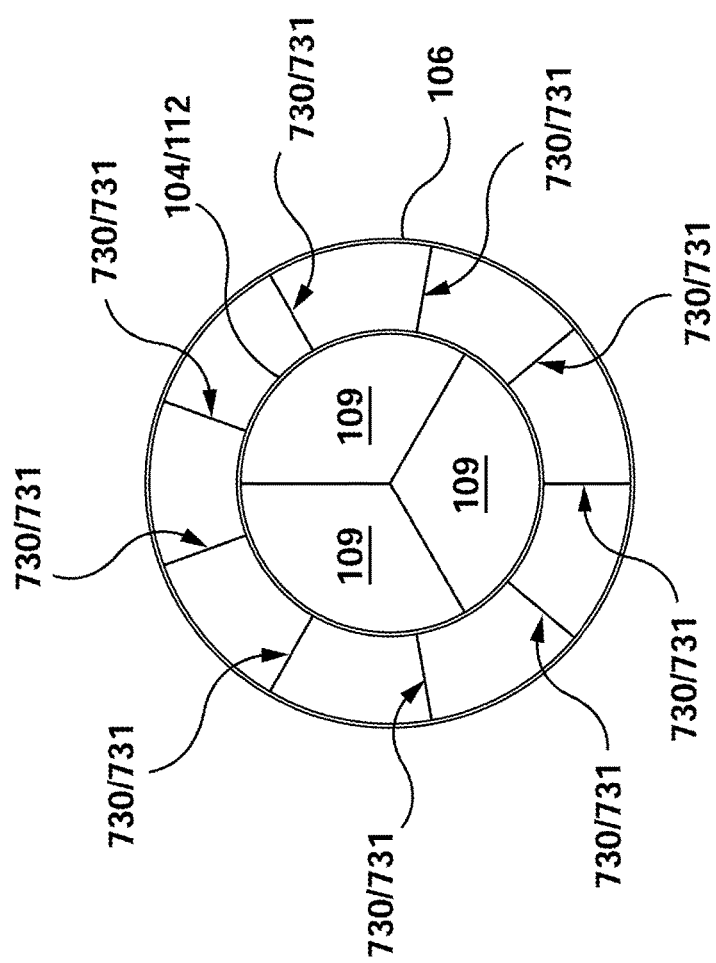
FIG. 8A
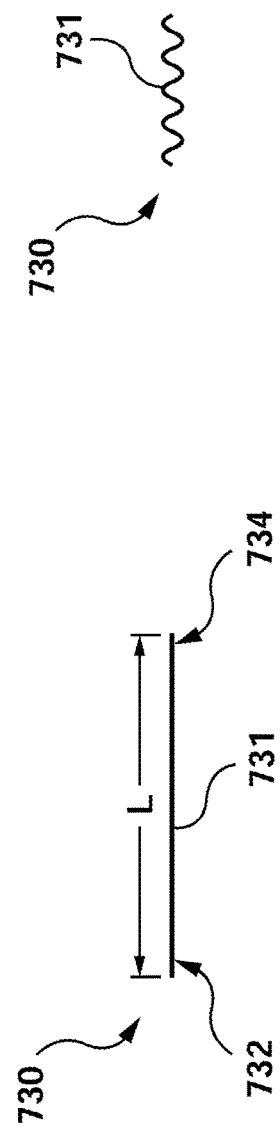
FIG. 9B
FIG. 9A

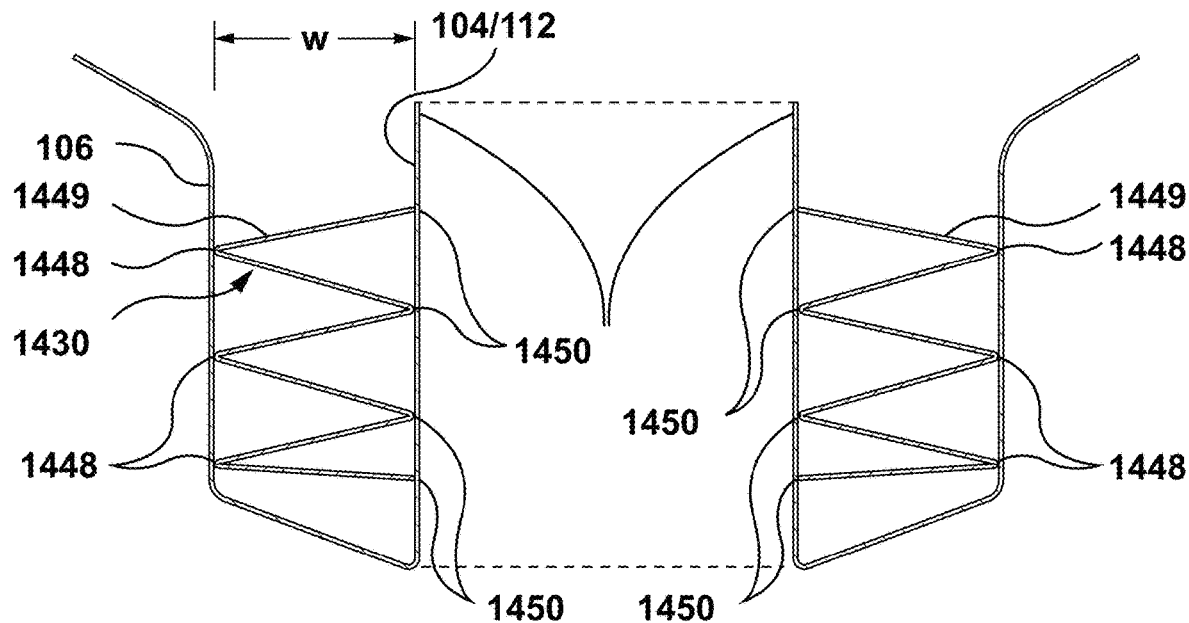
FIG. 14
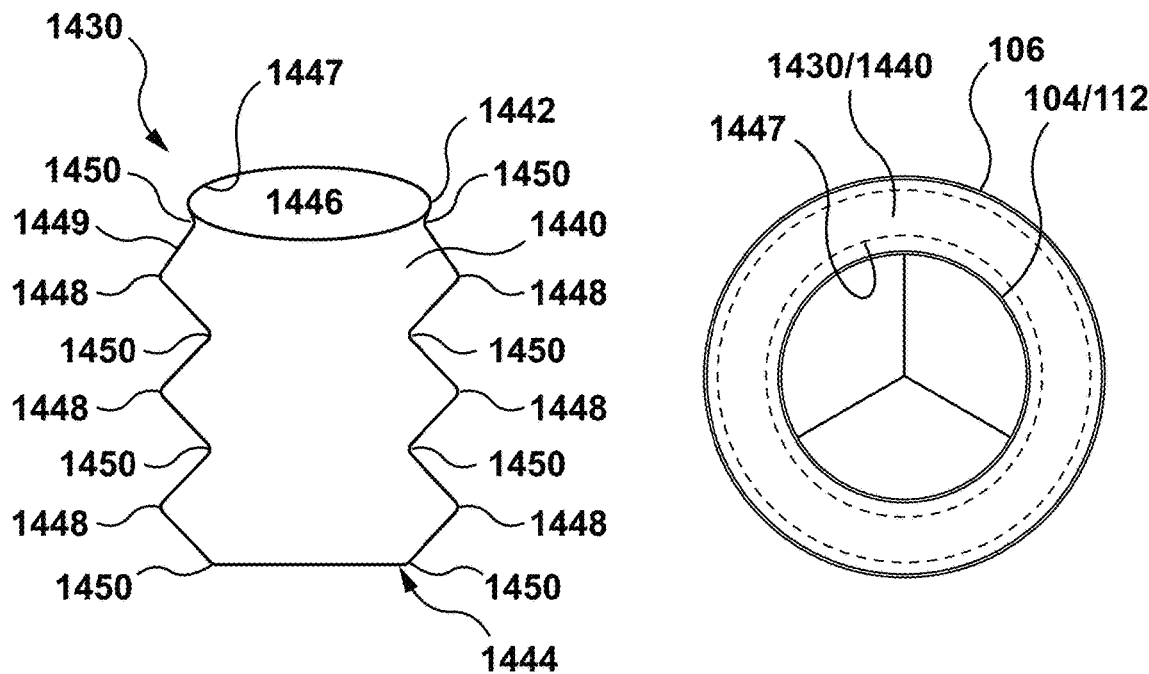 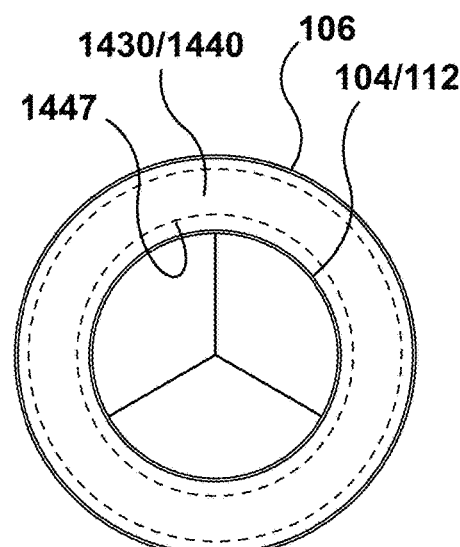
FIG. 15  FIG. 16

SKIRT-REINFORCEMENT MEMBERS FOR PROSTHETIC VALVE DEVICES

CROSS-REFERENCE TO RELATED APPLICATIONS

This application claims the benefit of U.S. Provisional Patent Application Ser. No. 63/152,982, filed Feb. 24, 2021, which is hereby incorporated by reference in its entirety for all purposes.

FIELD

The present technology is generally related to prosthetic valve devices, and in particular is directed to prosthetic valve devices including a skirt.

BACKGROUND

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs into systemic circulation. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The valve leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses are delivered in a radially compressed or crimped configuration so that the heart valve prosthesis can be advanced through the patient's vasculature. Once positioned at the treatment site, the heart valve prosthesis is expanded to engage tissue at the diseased heart valve region to, for instance, hold the heart valve prosthesis in position.

The present disclosure relates to improvements in a heart valve prosthesis to ensure that the heart valve prosthesis has a low profile for transcatheter delivery through a patient's vasculature.

SUMMARY

According to a first embodiment hereof, the present disclosure provides a prosthesis having a radially expanded configuration and a radially compressed configuration. The prosthesis includes an inner frame, an outer frame coupled to and radially surrounding the inner frame, an inner skirt coupled to a surface of the inner frame, and a flexible tether that spans between the outer frame and the inner skirt. The inner frame includes a plurality of crowns and a plurality of struts with each crown being formed between a pair of opposing struts, wherein a plurality of side openings is defined by the plurality of crowns and the plurality of struts. The inner skirt extends over at least one opening of the plurality of side openings of the inner frame. The flexible tether has a first end, a second end, and a length therebetween. The first end of the flexible tether is coupled to the outer frame and the second end of the flexible tether is directly attached to the inner skirt along an unsupported portion of the inner skirt that spans the at least one opening of the plurality of side openings of the inner frame.

In an aspect of the first embodiment, and in combination with any other aspects herein, the disclosure provides that the flexible tether is an elongated strand of suture material.

In an aspect of the first embodiment, and in combination with any other aspects herein, the disclosure provides that the length of the flexible tether is configured such that the flexible tether is under tension when the prosthesis is in the radially expanded configuration.

In an aspect of the first embodiment, and in combination with any other aspects herein, the disclosure provides that the first end of the flexible tether is directly attached to the outer frame.

In an aspect of the first embodiment, and in combination with any other aspects herein, the disclosure provides that an outer skirt is coupled to a surface of the outer frame, and the first end of the flexible tether is directly attached to the outer skirt.

In an aspect of the first embodiment, and in combination with any other aspects herein, the disclosure provides that at least one opening of the plurality of side openings is substantially diamond-shaped and is defined by a total of four struts.

In an aspect of the first embodiment, and in combination with any other aspects herein, the disclosure provides that each opening of the plurality of side openings is substantially diamond-shaped and is defined by a total of four struts.

In an aspect of the first embodiment, and in combination with any other aspects herein, the disclosure provides that a perimeter of the inner frame includes a row of side openings, the row including between six side openings and nine side openings.

In an aspect of the first embodiment, and in combination with any other aspects herein, the disclosure provides that the flexible tether is one of a plurality of flexible tethers that are circumferentially spaced apart from each other.

In an aspect of the first embodiment, and in combination with any other aspects herein, the disclosure provides that the inner skirt is coupled to an inner surface or an outer surface of the inner frame and the inner skirt extends over each opening of the plurality of side openings of the inner frame.

In an aspect of the first embodiment, and in combination with any other aspects herein, the disclosure provides that each of the inner frame and the outer frame is formed from a self-expanding material.

In an aspect of the first embodiment, and in combination with any other aspects herein, the disclosure provides that the prosthesis is a heart valve prosthesis and the prosthesis further comprises a prosthetic valve component disposed within and secured to the inner frame, the prosthetic valve being configured to block blood flow in one direction to regulate blood flow through a central lumen of the inner frame. In an embodiment, the heart valve prosthesis is configured for placement within a mitral heart valve or a tricuspid heart valve in situ.

According to a second embodiment hereof, the present disclosure provides a prosthesis having a radially expanded configuration and a radially compressed configuration. The prosthesis includes an inner frame, an outer frame coupled to and radially surrounding the inner frame, an inner skirt coupled to a surface of the inner frame, and a skirt-reinforcement member disposed between the outer frame and the inner skirt. The inner frame includes a plurality of crowns and a plurality of struts with each crown being formed between a pair of opposing struts, wherein a plurality of side openings is defined by the plurality of crowns and the plurality of struts. The inner skirt extends over at least one opening of the plurality of side openings of the inner frame. The skirt-reinforcement member is a tubular body having a series of alternating pleats defining circumferential out-folds and circumferential in-folds along a length of the tubular body. The circumferential out-folds of the tubular body are coupled to the outer frame and the circumferential in-folds of the tubular body are directly attached to the inner skirt along an unsupported portion of the inner skirt that spans the at least one opening of the plurality of side openings of the inner frame.

In an aspect of the second embodiment, and in combination with any other aspects herein, the disclosure provides that the circumferential out-folds of the tubular body are coupled to the outer frame at a plurality of outer connection points and the circumferential in-folds of the tubular body are attached to the inner skirt at a plurality of inner connection points, each inner connection point being along an unsupported portion of the inner skirt.

In an aspect of the second embodiment, and in combination with any other aspects herein, the disclosure provides that each pleat has a width between a circumferential in-fold and a circumferential out-fold, the width being configured such that the pleat of the skirt-reinforcement member is under tension when the prosthesis is in the radially expanded configuration.

In an aspect of the second embodiment, and in combination with any other aspects herein, the disclosure provides that the circumferential out-folds of the tubular body are directly attached to the outer frame.

In an aspect of the second embodiment, and in combination with any other aspects herein, the disclosure provides that an outer skirt is coupled to a surface of the outer frame, and the circumferential out-folds of the tubular body are directly attached to the outer skirt.

In an aspect of the second embodiment, and in combination with any other aspects herein, the disclosure provides that at least one opening of the plurality of side openings is substantially diamond-shaped and is defined by a total of four struts.

In an aspect of the second embodiment, and in combination with any other aspects herein, the disclosure provides that each opening of the plurality of side openings is substantially diamond-shaped and is defined by a total of four struts.

In an aspect of the second embodiment, and in combination with any other aspects herein, the disclosure provides that a perimeter of the inner frame includes a row of side openings, the row including between six side openings and nine side openings.

In an aspect of the second embodiment, and in combination with any other aspects herein, the disclosure provides that the tubular body has a first end, a second end, and a length therebetween and the length of the tubular body is less than a length of the inner frame.

In an aspect of the second embodiment, and in combination with any other aspects herein, the disclosure provides that the inner skirt is coupled to an inner surface or an outer surface of the inner frame and the inner skirt extends over each opening of the plurality of side openings of the inner frame.

In an aspect of the second embodiment, and in combination with any other aspects herein, the disclosure provides that each of the inner frame and the outer frame is formed from a self-expanding material.

In an aspect of the second embodiment, and in combination with any other aspects herein, the disclosure provides that the prosthesis is a heart valve prosthesis and the prosthesis further comprises a prosthetic valve component disposed within and secured to the inner frame, the prosthetic valve being configured to block blood flow in one direction to regulate blood flow through a central lumen of the inner frame. In an embodiment, the heart valve prosthesis is configured for placement within a mitral heart valve or a tricuspid heart valve in situ.

According to a third embodiment hereof, the present disclosure provides a prosthesis having a radially expanded configuration and a radially compressed configuration. The prosthesis includes an inner frame, an outer frame coupled to and radially surrounding the inner frame, and a plurality of toroidal components disposed between the outer frame and the inner frame. The inner frame includes a plurality of crowns and a plurality of struts with each crown being formed between a pair of opposing struts, wherein a plurality of side openings is defined by the plurality of crowns and the plurality of struts. Each toroidal component of the plurality of toroidal components has an outer circumferential surface and an inner circumferential surface. The outer circumferential surface of each toroidal component is directly attached to the outer frame and the inner circumferential surface of each toroidal component is directly attached to the inner frame. The inner circumferential surface extends over the plurality of side openings of the inner frame.

In an aspect of the third embodiment, and in combination with any other aspects herein, the disclosure provides that each toroidal component has a width between the outer circumferential surface and the inner circumferential surface, the width being configured such that each toroidal component is under tension when the prosthesis is in the radially expanded configuration.

In an aspect of the third embodiment, and in combination with any other aspects herein, the disclosure provides that the outer circumferential surfaces of the plurality of toroidal components collectively form an impermeable skirt on the outer frame and the inner circumferential surfaces of the plurality of toroidal components collectively form an impermeable skirt on the inner frame.

In an aspect of the third embodiment, and in combination with any other aspects herein, the disclosure provides that each opening of the plurality of side openings is substantially diamond-shaped and is defined by a total of four struts.

In an aspect of the third embodiment, and in combination with any other aspects herein, the disclosure provides that a perimeter of the inner frame includes a row of side openings, the row including between six side openings and nine side openings.

In an aspect of the third embodiment, and in combination with any other aspects herein, the disclosure provides that the plurality of toroidal components collectively extend an entire length of the inner frame.

In an aspect of the third embodiment, and in combination with any other aspects herein, the disclosure provides that each of the inner frame and the outer frame is formed from a self-expanding material.

In an aspect of the third embodiment, and in combination with any other aspects herein, the disclosure provides that the prosthesis is a heart valve prosthesis and the prosthesis further comprises a prosthetic valve component disposed within and secured to the inner frame, the prosthetic valve being configured to block blood flow in one direction to regulate blood flow through a central lumen of the inner frame. In an embodiment, the heart valve prosthesis is configured for placement within a mitral heart valve or a tricuspid heart valve in situ.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 8A depicts a simplified illustration of a top view of FIG. 7, wherein the transcatheter valve prosthesis is in its radially expanded configuration.

FIG. 8B depicts a simplified illustration of a top view of FIG. 7, wherein the transcatheter valve prosthesis is in its radially compressed configuration.

FIG. 9A depicts a skirt-reinforcement member of FIG. 7 removed from the transcatheter valve prosthesis for sake of illustration only, wherein the skirt-reinforcement member is shown in a linear or straight configuration which corresponds to the transcatheter valve prosthesis in its radially expanded configuration.

FIG. 9B depicts a skirt-reinforcement member of FIG. 7 removed from the transcatheter valve prosthesis for sake of illustration only, wherein the skirt-reinforcement member is shown in a slackened configuration which corresponds to the transcatheter valve prosthesis in its radially compressed configuration.

FIG. 14 is a cross-sectional view according to another embodiment hereof, wherein the transcatheter valve prosthesis is in its radially expanded configuration and wherein the transcatheter valve prosthesis further includes a tubular skirt-reinforcement member in accordance with an aspect of the disclosure.

FIG. 15 is a side view of the tubular skirt-reinforcement member of FIG. 14, wherein the tubular skirt-reinforcement member is removed from the transcatheter valve prosthesis for sake of illustration only.

FIG. 16 is a simplified illustration of a top view of FIG. 14, with the tubular skirt-reinforcement member being shown in phantom to depict placement thereof for sake of illustration only.

DETAILED DESCRIPTION

Figure 1:
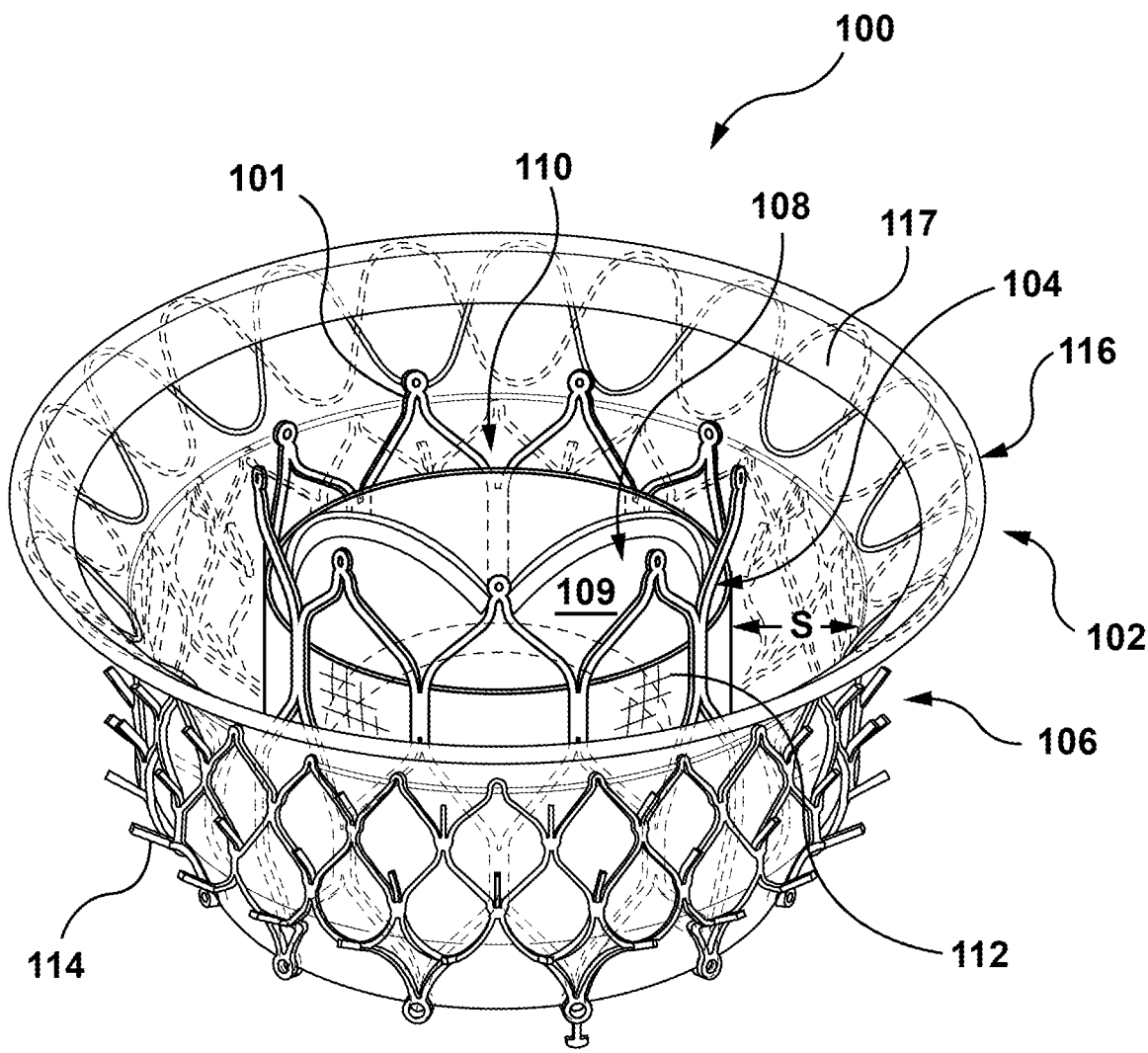
FIG. 1 depicts a perspective view of a transcatheter valve prosthesis in accordance with an aspect of the disclosure.

Specific embodiments of the present invention are now described with reference to the figures, wherein like reference numbers indicate identical or functionally similar elements. The terms "distal" and "proximal," when used in the following description to refer to a native vessel, native valve, or a device to be implanted into a native vessel or native valve, such as a transcatheter valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

Embodiments hereof relate to a skirt-reinforcement member for supporting or reinforcing a skirt that spans across a side opening of a stent or frame of a valve prosthesis. The skirt-reinforcement member provides the valve prosthesis with a reinforced skirt having long-lasting durability and superior implant performance. In addition, as will be explained in more detail herein, the skirt-reinforcement member is configured to prevent billowing of the skirt material that spans across the side opening of the inner frame of the valve prosthesis, as such billowing may undesirably result in contact between the skirt and the leaflets of the valve prosthesis after the valve prosthesis is deployed in situ. If the leaflets of the valve prosthesis contact the skirt during opening and closing in situ, such contact may cause early leaflet tissue abrasion as well as early skirt abrasion due to the undesired billowing of the skirt. Additionally, the greater relative motion between the skirt and the inner frame may further induce early skirt abrasion. Early leaflet tissue abrasion and/or early skirt abrasion has a negative impact on the long-term durability of the valve prosthesis. The skirt-reinforcement members disclosed herein reinforce the material of the skirt that spans across the side opening of the inner frame of the valve prosthesis to limit the radial motion or billowing of the skirt material, thereby minimizing risk of damage to both the skirt and the leaflets. In embodiments hereof, the skirt-reinforcement members reinforce the material of a skirt that spans across the side opening of an inner frame of the valve prosthesis using connections between the material of the skirt and an outer frame of the valve prosthesis.

FIGS. 1-6 illustrate a transcatheter valve prosthesis 100 that may be utilized with embodiments of skirt-reinforcement members described herein. The transcatheter valve prosthesis 100 is illustrated herein in order to facilitate description of the present invention. The following description of the transcatheter valve prosthesis 100 is merely exemplary in nature and is not intended to limit the invention or the application and uses of the invention. It is understood that any number of alternate heart valve prostheses can be used with the skirt-reinforcement members described herein. Other non-limiting examples of transcatheter heart valve prostheses that can be used with the skirt-reinforcement members described herein are described in U.S. application Ser. No. 16/853,851 to McVeigh et al., U.S. Pat. No. 9,034,032 to McLean et al. and International Patent Application No. PCT/US2014/029549 to McLean et al, each of which is incorporated by reference herein in its entirety. Although the transcatheter valve prosthesis 100 is a heart valve prosthesis configured for placement within a mitral heart valve or a tricuspid heart valve, embodiments of skirt-reinforcement members described herein may be utilized with any dual frame prosthesis (i.e., a prosthesis having an inner frame and an outer frame coupled to and radially surrounding the inner frame) having a skirt. For example, embodiments of skirt-reinforcement members described herein may be utilized with a transcatheter heart valve configured for placement within a pulmonary, aortic, mitral, or tricuspid valve, or may be utilized with a transcatheter valve prosthesis configured for placement within a venous valve or within other body passageways where it is deemed useful. There is no intention to be bound by any expressed or implied theory presented in the preceding technical field, background, brief summary or the following detailed description. In addition, embodiments of skirt-reinforcement members described herein may be utilized with any dual frame prosthesis (i.e., a prosthesis having an inner frame and an outer frame coupled to and radially surrounding the inner frame) having an inner skirt for which reinforcement thereof is desirable to limit billowing, and it is not required that the stent or frame include a prosthetic valve component disposed therein.

A perspective view of the transcatheter valve prosthesis 100 in accordance with an aspect of the disclosure is shown in FIG. 1. The transcatheter valve prosthesis 100 is configured to be radially compressed into a reduced-diameter crimped configuration for delivery within a vasculature (not shown) and to return to an expanded, deployed configuration, as shown in FIG. 1. Stated another way, the transcatheter valve prosthesis 100 has a crimped configuration for delivery within a vasculature and an expanded configuration for deployment within a native heart valve. In accordance with embodiments hereof, when in the crimped configuration, the transcatheter valve prosthesis 100 has a low profile suitable for delivery to and deployment within a native heart valve via a suitable delivery catheter that may be tracked to the deployment site of the native heart valve of a heart via any one of a transseptal, retrograde, or transapical approach. The transcatheter valve prosthesis 100 includes a stent or dual frame 102 and a prosthetic valve component 108 including at least one leaflet disposed within and secured to the dual frame 102.

Any portion of the dual frame 102 described herein as an element of a heart valve prosthesis 100 may be made from any number of suitable biocompatible materials, e.g., stainless steel, nickel titanium alloys such as Nitinol™, cobalt chromium alloys such as MP35N, other alloys such as ELGILOY® (Elgin, Ill.), various polymers, pyrolytic carbon, silicone, polytetrafluoroethylene (PTFE), or any number of other materials or combination of materials. A suitable biocompatible material would be selected to provide the transcatheter heart valve prosthesis 100 to be configured to be compressed into a reduced-diameter crimped configuration for transcatheter delivery to a native valve, whereby release from a delivery catheter returns the prosthesis to an expanded, deployed configuration.

In an aspect of the disclosure, the dual frame 102 of the transcatheter valve prosthesis 100 includes a valve support or inner frame 104 at least partially surrounded by and coupled to an anchor element or outer frame 106. The inner frame 104 is a tubular stent structure that defines a central lumen 110 from an inflow end 101 of the inner frame 104 to an outflow end 103 of the inner frame 104. The inner frame 104 is configured to support the prosthetic valve component 108 therein, which will be described in more detail below. In an embodiment, the inner frame 104 has a substantially cylindrical shape in which the outflow end 103 of the inner frame 104 has a diameter that is substantially the same as a diameter of the inflow end 101 of the inner frame 104.

The inner frame 104 includes an inner skirt 112 coupled to a surface thereof. More particularly, the inner skirt 112 is coupled to an inner surface of the inner frame 104 to line a portion thereof. Alternatively, the inner skirt 112 may be coupled to an outer surface of the inner frame 104 to enclose a portion thereof as would be known to one of ordinary skill in the art of prosthetic valve construction. The inner skirt 112 may be a natural or biological material such as pericardium or another membranous tissue such as intestinal submucosa. Alternatively, the inner skirt 112 may be a low-porosity woven fabric, such as polyester, Dacron fabric, or PTFE, which creates a one-way fluid passage when attached to the stent. In one embodiment, the inner skirt 112 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

In an aspect of the disclosure, the outer frame 106 is a tubular stent structure that functions as an anchor for the transcatheter valve prosthesis 100 to secure its deployed position within a native annulus. The outer frame 106 is a substantially cylindrically-shaped structure that is configured to engage heart tissue at or below an annulus of a native heart valve, such as an annulus of a native mitral valve or native tricuspid valve. At the inflow end 101 of the inner frame 104, the outer frame 106 is radially spaced a distance S from the inner frame 104 to mechanically isolate the inflow end 101 of the inner frame 104 from the outer frame 106. The outer frame 106 includes one or more cleats or prongs 114 that extend outward from an exterior side thereof to engage heart tissue. In another embodiment, the outer frame 106 may employ barbs, spikes, or other tissue fixation mechanisms for engaging heart tissue.

The transcatheter valve prosthesis 100 further includes a brim or rim element 116 that extends outwardly from an upstream end of the outer frame 106. The brim element 116 includes overlapping, 180 degree out of phase sinusoidal wire forms that are attached and hinged to the outer frame 106 by a suitable biocompatible low-profile fabric 117 used in bioprosthetic implants namely endovascular grafts, heart valves or left atrial appendage devices to promote bio-integration, such as woven polyethylene terephthalate (PET) fabric. The brim element 116 may act as an atrial retainer, if present, and to serve such a function the brim element 116 may be configured to engage tissue above a native annulus, such as a supra-annular surface or some other tissue in the left atrium, to thereby inhibit downstream migration of a prosthetic heart valve 100, for e.g., during atrial systole.

Figure 2:
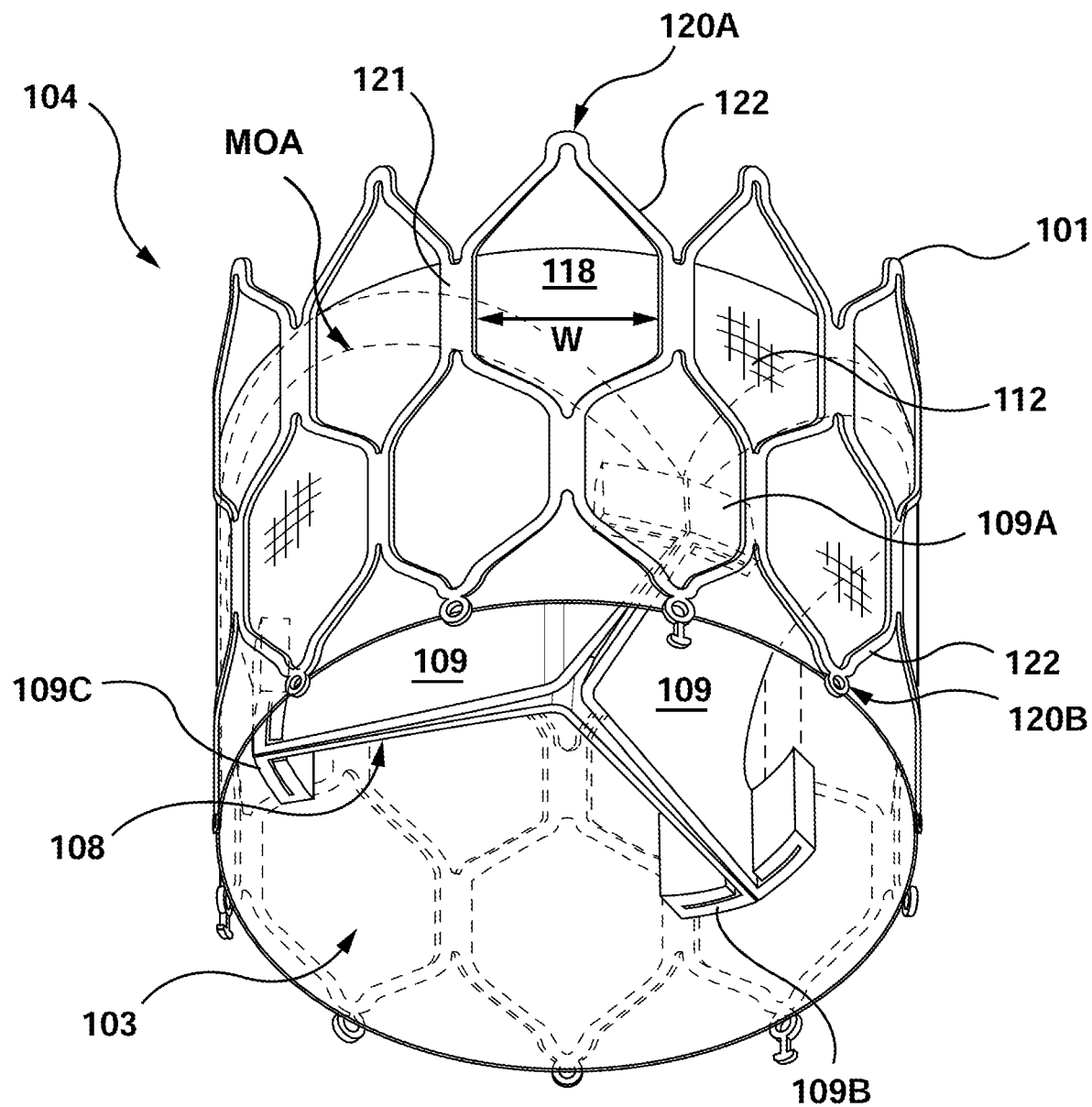
FIG. 2 depicts a perspective view of a valve support of the transcatheter valve prosthesis of FIG. 1 with a prosthetic valve component secured therein in accordance with an aspect of the disclosure.
Figure 4:
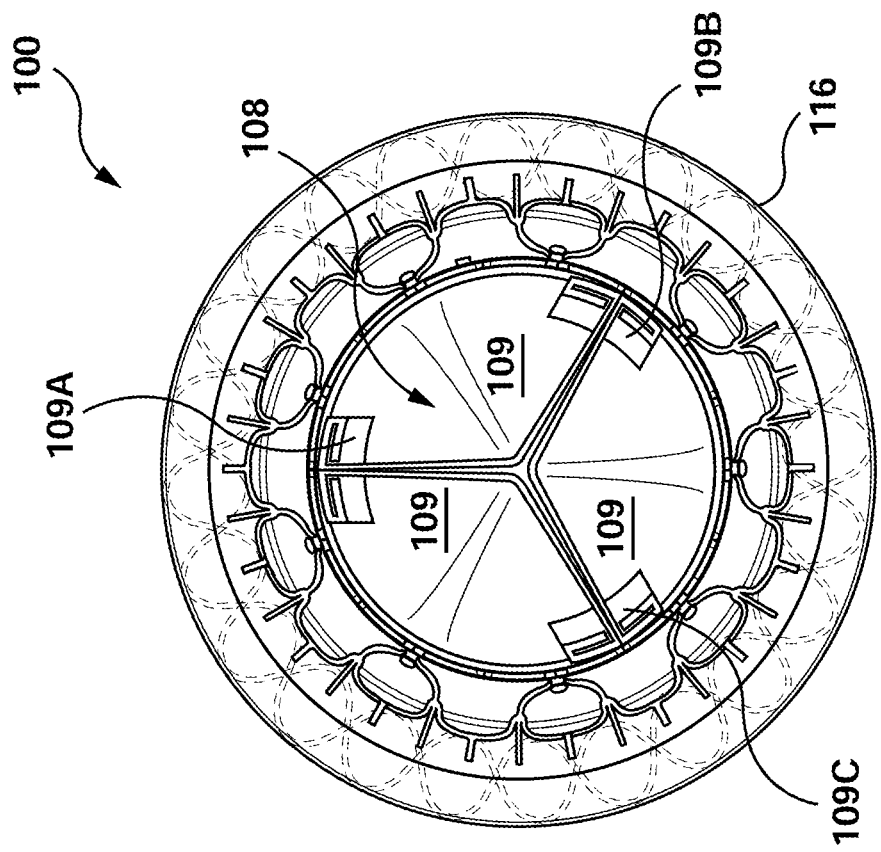
FIG. 4 depicts a ventricular or outflow end view of the transcatheter valve prosthesis shown in FIG. 1 in accordance with an aspect of the disclosure.
Figure 3:
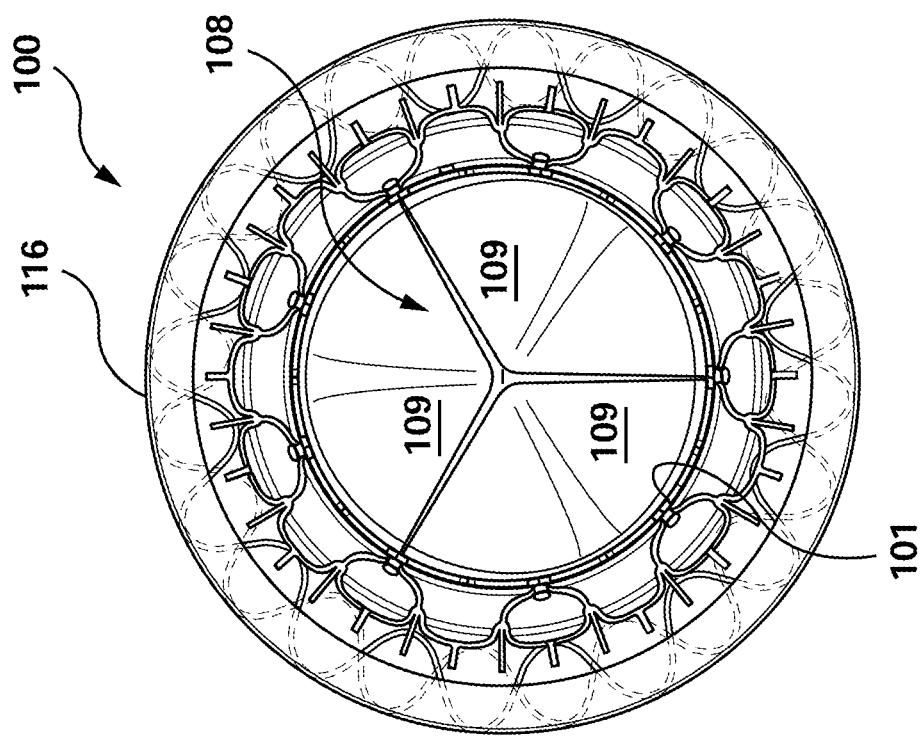
FIG. 3 depicts an atrial or inflow end view of the transcatheter valve prosthesis shown in FIG. 1 in accordance with an aspect of the disclosure.

The prosthetic valve component 108 of the transcatheter valve prosthesis 100 is capable of regulating flow therethrough via valve leaflets that may form a replacement valve. FIGS. 1-6 illustrate an exemplary prosthetic valve component having three leaflets, although a single leaflet or bicuspid leaflet configuration may alternatively be used in embodiments hereof. When deployed in situ, the prosthetic valve component 108 in a closed state is configured to block blood flow in one direction to regulate blood flow through the central lumen 110 of the inner frame 104. FIG. 2 depicts a perspective view of the inner frame 104 with a prosthetic valve component 108 secured therein, the inner frame 104 being shown in FIG. 2 removed from the remainder of the transcatheter valve prosthesis 100 shown in FIG. 1 for ease of illustration. FIG. 3 depicts an atrial or inflow end view of the transcatheter valve prosthesis 100 shown in FIG. 1, and FIG. 4 depicts a ventricular or outflow end view of the transcatheter valve prosthesis 100 shown in FIG. 1. The prosthetic valve component 108 includes valve leaflets 109, e.g., three valve leaflets 109, that are disposed to coapt within an upstream portion of the inner frame 104 with leaflet commissures 109A, 109B, 109C of the valve leaflets 109 being secured within a downstream portion of the inner frame 104, such that the valve leaflets 109 open during diastole. Leaflets 109 are attached along their bases to the inner frame 104, for example, using sutures or a suitable biocompatible adhesive. A margin of attachment, or MOA, is formed at the junction of the leaflets 109 to the inner frame 104. Adjoining pairs of leaflets 109 are attached to one another at their lateral ends to form leaflet commissures 109A, 109B, 109C. The orientation of the leaflets 109 within the inner frame 104 depends upon on which end of the transcatheter valve prosthesis 100 is the inflow end and which end of the transcatheter valve prosthesis 100 is the outflow end, thereby ensuring one-way flow of blood through the transcatheter valve prosthesis 100.

The valve leaflets 109 may be attached to the inner skirt 112. The valve leaflets 109 may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

For delivery, the transcatheter valve prosthesis 100 is radially compressed into a reduced-diameter crimped configuration onto a delivery system for delivery within a vasculature. As known in the art, the delivery system includes an inner shaft that receives the transcatheter valve prosthesis 100 on a distal portion thereof and an outer sheath or capsule that is configured to compressively retain the transcatheter valve prosthesis 100 on the distal portion of the inner shaft during delivery. Stated another way, the outer sheath or capsule surrounds and constrains the transcatheter valve prosthesis 100 in the radially compressed or crimped configuration. An exemplary delivery system for delivering the transcatheter valve prosthesis 100 is described in U.S. Pat. No. 9,034,032 to McLean et al. and International Patent Application No. PCT/US2014/029549 to McLean et al, previously incorporated by reference as if set forth fully herein. However, it will be apparent to one of ordinary skill in the art that other delivery systems may be utilized and that the components of the delivery system may vary depending upon the configuration and structure of the transcatheter valve prosthesis that is being delivered.

Figure 5:
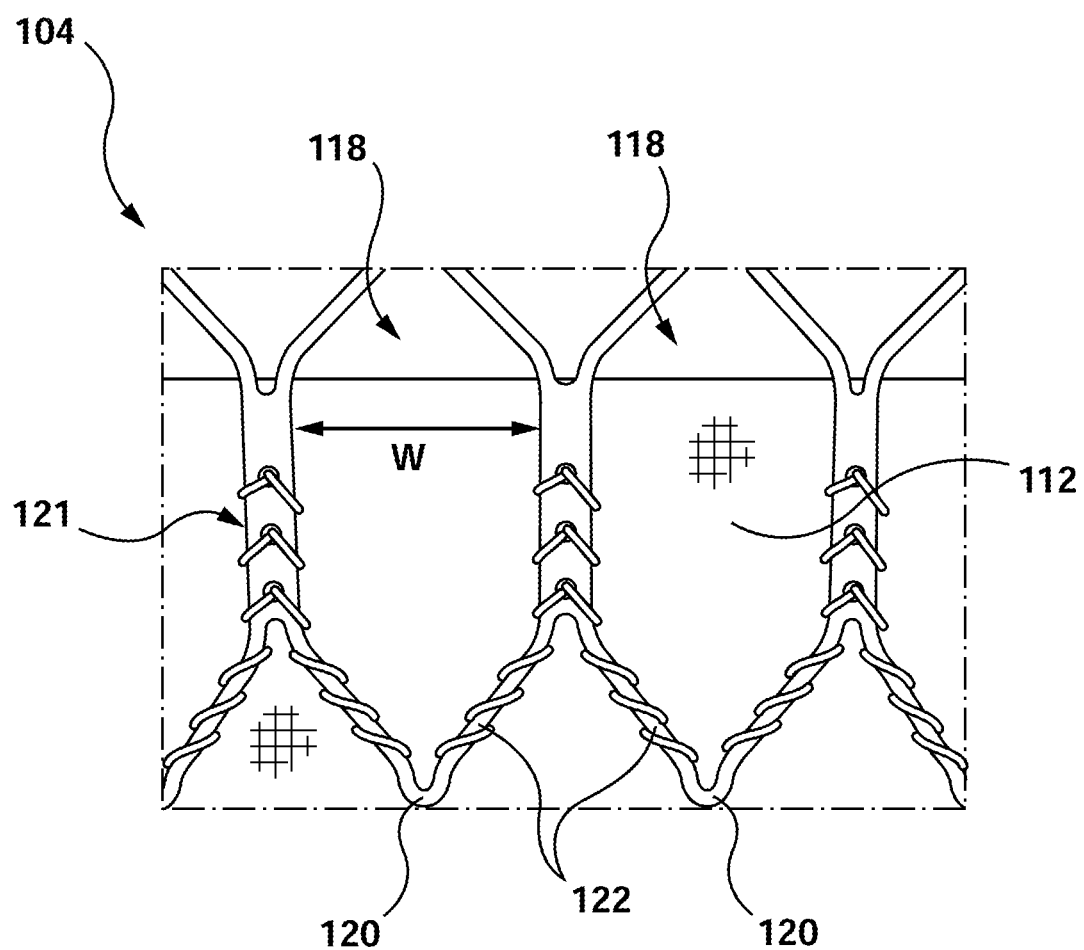
FIG. 5 is an enlarged side view of a side opening of the valve support of FIG. 2.

Referring to FIG. 2 as well as FIG. 5, the structure of the inner frame 104 will now be described in more detail. FIG. 5 is an enlarged side view of a plurality of side openings 118 of the inner frame 104. The inner frame 104 includes a plurality of crowns 120 and a plurality of struts 122 with each crown 120 being formed between a pair of opposing struts 122. Each crown 120 is a curved segment or bend extending between opposing struts 122. The inner frame 104 is tubular, with the plurality of side openings 118 being defined by edges of the plurality of crowns 120 and the plurality of struts 122. In an embodiment, the plurality of side openings 118 may be substantially diamond-shaped. The inner frame 104 includes a plurality of nodes 121. A node 121 is defined as a region where two crowns of the plurality of crowns 120 within the inner frame 104 meet or connect. As best shown in FIG. 5, in this embodiment, the inner skirt 112 is attached to an inner surface of the inner frame 104 around a circumference thereof. The inner skirt 112 lines the inner surface of the inner frame 104 and spans across or extends over each side opening 118 of the plurality of side openings 118. Notably, as shown in FIG. 5, it is not required that the inner skirt 112 extend over the full opening of each side opening 118. Rather, the inner skirt 112 may span or cover only a portion of the side opening 118 as shown in FIG. 5.

A series of endmost inflow crowns 120A are formed at the inflow end 101 of the inner frame 104, and a series of endmost outflow crowns 120B are formed at the outflow end 103 of the inner frame 104. In an embodiment, the inflow end 101 of the inner frame 104 has a total of nine endmost inflow crowns 120A around a circumference thereof. The inflow end 101 of the inner frame 104 includes a row of side openings 118 around a circumference thereof, and the row has a total of nine side openings 118. Further, outflow end 103 of the inner frame 104 has a total of nine endmost inflow crowns 120B around a circumference thereof. The outflow end 103 of the inner frame 104 includes a row of side openings 118 around a circumference thereof, and the row has a total of nine side openings 118. In another embodiment hereof (not shown), each of the inflow end 101 and the outflow end 103 of the inner frame 104 has between six and nine endmost inflow crowns 120A, 120B around a circumference thereof and includes the row of side openings 118 around a circumference thereof that includes between six and nine side openings 118.

A width W of the side openings 118 is relatively wider as compared to other stents or frames known in the art, thereby resulting a relatively lower total of side openings 118 around a circumference of the inner frame 104. In an embodiment, width W is between $1/24^{th}$ and $1/6^{th}$ of the circumference of the inner frame 104, or stated another way, between 4% and 16% of the circumference of the inner frame 104. By increasing the width of the side openings 118, a lesser amount of material may be required for the inner frame 104 such that a lower profile may be achieved when the inner frame 104 is crimped into a radially compressed configuration for delivery. More particularly, since the dual frame 102 includes both the inner frame 104 and the outer frame 106, it is a challenge to reduce the profile of the transcatheter valve prosthesis 100 in the crimped or radially compressed configuration. The challenge with reducing the profile is that, in the crimped or radially compressed configuration, the incompressible material of the dual frame 102 imparts high compressive forces on the soft tissue material of the leaflets 109. Such high compressive forces may alter the integrity of the leaflets 109, thereby impacting the long-term durability of the transcatheter valve prosthesis 100. However, increasing the width W of the side openings 118 provides a reduction of the incompressible material of the dual frame 102, thereby enabling a lower profile in the crimped or radially compressed configuration.

Figure 6A:
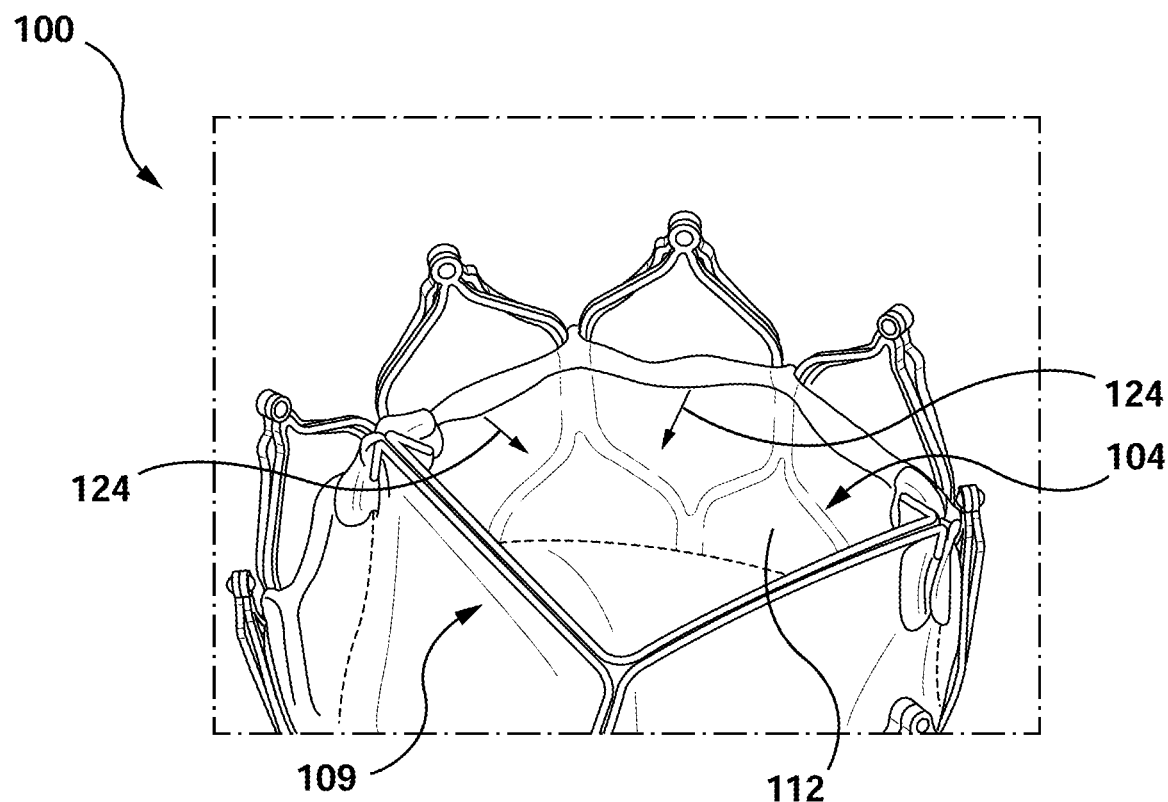
FIG. 6A is a perspective atrial end view of the transcatheter valve prosthesis shown in FIG. 1 in accordance with an aspect of the disclosure.
Figure 6B:
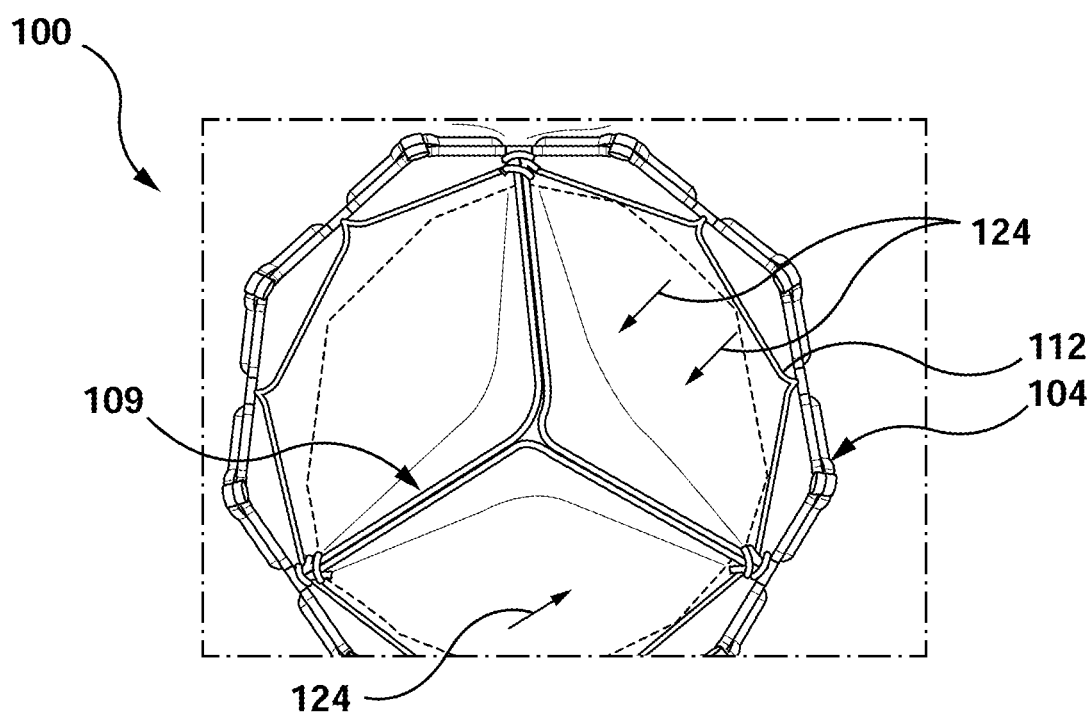
FIG. 6B is an atrial end view of the transcatheter valve prosthesis shown in FIG. 1 in accordance with an aspect of the disclosure.

However, reducing the incompressible material of the dual frame 102 means that the inner skirt 112 spans a longer distance between nodes 121 or between struts 122. Stated another way, with the width of the side openings 118 being relatively increased as described above, the amount of material of the inner skirt 112 that spans across the side openings 118 likewise increases and thus a greater amount of material of the inner skirt 112 is unattached to or unsupported by the inner frame 104. Referring now to FIGS. 6A and 6B, when an increased amount of material of the inner skirt 112 spans across the side openings 118, there is an increased chance of the inner skirt 112 billowing or moving radially inwards towards the leaflets 109 as indicated by directional arrows 124. The inner skirt 112 may billow during valve opening and closing in situ, and the leaflets 109 may contact the inner skirt 112. Such billowing may undesirably result in contact between the inner skirt 112 and the leaflets 109 of the transcatheter valve prosthesis 100. If the leaflets 109 of the transcatheter valve prosthesis 100 contact the inner skirt 112 during opening and closing, such contact may cause early leaflet tissue abrasion as well as early skirt abrasion. Additionally, the greater relative motion between the inner skirt 112 and the inner frame 104 may further induce early skirt abrasion.

Embodiments hereof relate to skirt-reinforcement members that reinforce the material of the inner skirt 112 that spans across the side openings 118 of the inner frame 104 to limit the radial motion or billowing of the skirt material, thereby minimizing risk of damage to both the inner skirt 112 and the leaflets 109. For sake of illustration, the skirt-reinforcement members described herein are incorporated onto the transcatheter valve prosthesis 100, as the structure of the transcatheter valve prosthesis 100 has already been described in detail above. However, the skirt-reinforcements members described herein may be incorporated onto any dual frame prosthesis (i.e., a prosthesis having an inner frame and an outer frame coupled to and radially surrounding the inner frame) having an inner skirt for which reinforcement thereof is desirable to limit billowing, and it is not required that the stent or frame include a prosthetic valve component disposed therein.

Figure 7:
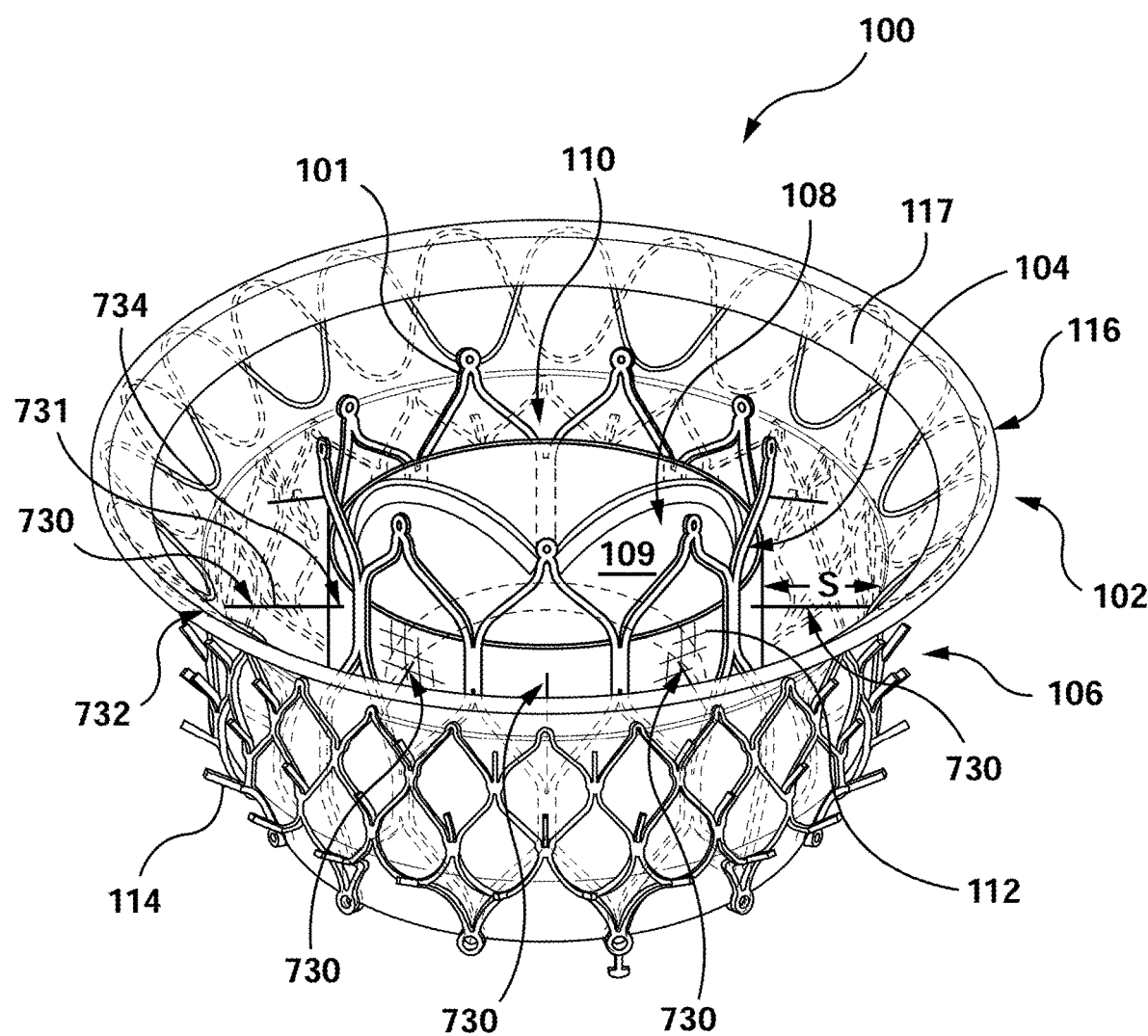
FIG. 7 is a perspective view of the transcatheter valve prosthesis of FIG. 1, wherein the transcatheter valve prosthesis is in its radially expanded configuration and wherein the transcatheter valve prosthesis further includes a plurality of skirt-reinforcement members in accordance with an aspect of the disclosure.
Figure 10:
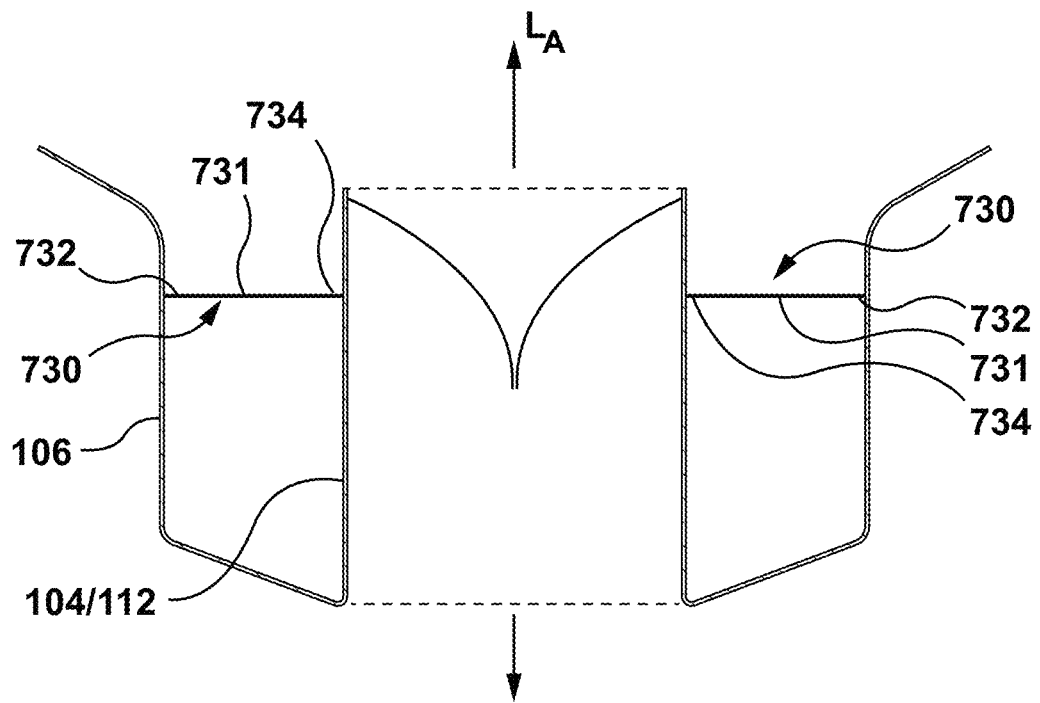
FIG. 10 is a cross-sectional view of FIG. 7, wherein the transcatheter valve prosthesis is in its radially expanded configuration.

Turning to FIGS. 7-10, a skirt-reinforcement member 730 according to an aspect of the disclosure is illustrated. FIG. 7 is a perspective view of the transcatheter valve prosthesis 100 in its radially expanded configuration, and the transcatheter valve prosthesis 100 further includes a plurality of skirt-reinforcement members 730. FIG. 8A depicts a simplified illustration of a top view of FIG. 7 with the transcatheter valve prosthesis 100 in its radially expanded configuration, and FIG. 8B depicts a simplified illustration of a top view of FIG. 7 with the transcatheter valve prosthesis 100 is in its radially compressed configuration. FIG. 9A and FIG. 9B depict a skirt-reinforcement member of FIG. 7 removed from the transcatheter valve prosthesis for sake of illustration only. The skirt-reinforcement member is shown in a linear or straight configuration in FIG. 9A which corresponds to the transcatheter valve prosthesis in its radially expanded configuration, and the skirt-reinforcement member is shown in a slackened configuration in FIG. 9B which corresponds to the transcatheter valve prosthesis in its radially compressed configuration. FIG. 10 is a cross-sectional view of FIG. 7 with the transcatheter valve prosthesis 100 is in its radially expanded configuration.

Each skirt-reinforcement member 730 is a flexible tether that spans or extends between the outer frame 106 and the inner skirt 112. In an embodiment, each skirt-reinforcement member 730 is an elongated filament or strand 731 of suture. Exemplary suture materials include but are not limited to a monofilament or plastic suture material, such as polypropylene. In an embodiment, each skirt-reinforcement member 730 is a thin pre-shaped wire of a shape memory alloy such as NITINOL, the thin wire having a diameter size similar to a suture material. Each skirt-reinforcement member 730 is configured to restrict or prevent billowing, or radial motion, of an unsupported portion of the inner skirt 112 that spans across or extends over a respective side opening 118. As used herein, "unsupported portion of the skirt" refers to areas of the inner skirt 112 in which a surface of the inner skirt does not directly contact or abut against the inner frame 104. Each skirt-reinforcement member 730 has a first end 732, a second end 734, and a length L therebetween. The first end 732 of each skirt-reinforcement member 730 is coupled to the outer frame 106 and the second end 734 of each skirt-reinforcement member 730 is directly attached to the inner skirt 112 along the unsupported portion of the inner skirt 112 that spans one or more of the plurality of side openings 118 of the inner frame 104. Since the first end 732 is coupled to the outer frame 106, the skirt-reinforcement member 730 applies tension to the inner skirt 112 and thereby prevents undesired billowing of the skirt material. The skirt-reinforcement member 730 is formed from a flexible material such that it is configured to slacken when the transcatheter valve prosthesis 100 is in its radially compressed configuration, but is configured to be under tension when the transcatheter valve prosthesis 100 is in its radially expanded configuration, thereby mitigating movement of the inner skirt 112 throughout the cardiac cycle.

Figure 12:
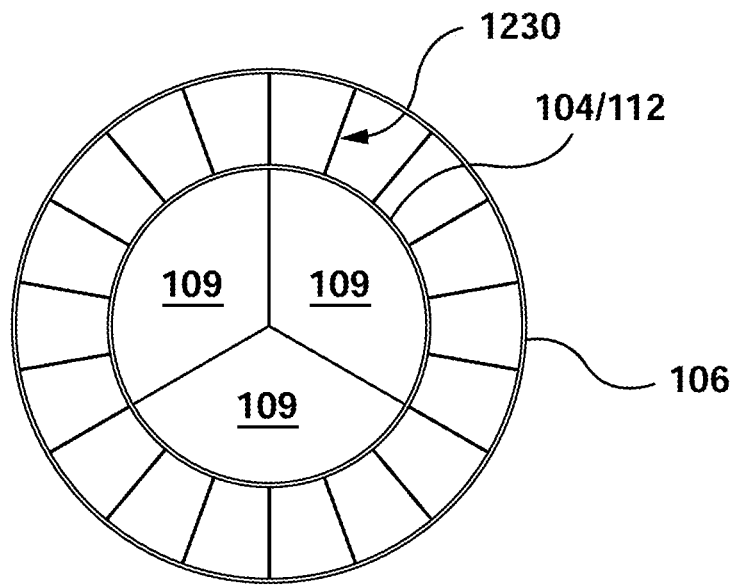
FIG. 12 depicts a simplified illustration of a top view according to another embodiment hereof, wherein the transcatheter valve prosthesis is in its radially expanded configuration and wherein the transcatheter valve prosthesis further includes a plurality of skirt-reinforcement members in accordance with an aspect of the disclosure.
Figure 13:
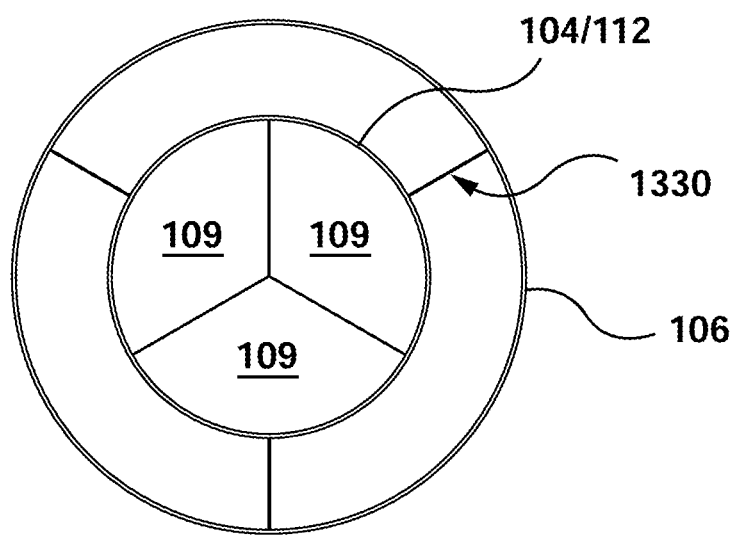
FIG. 13 depicts a simplified illustration of a top view according to another embodiment hereof, wherein the transcatheter valve prosthesis is in its radially expanded configuration and wherein the transcatheter valve prosthesis further includes a plurality of skirt-reinforcement members in accordance with an aspect of the disclosure.

In the embodiment of FIGS. 7-10, the inner frame 104 includes a row of side openings 118 around a circumference thereof and a skirt-reinforcement member 730 is directly attached to skirt material of each side opening 118 of the row of side openings 118 around the circumference of the inner frame 104. Thus, as the row includes a total of nine side openings 118 around the circumference of the inner frame 104, the transcatheter valve prosthesis 100 includes a total of nine skirt-reinforcement members 730. The plurality of skirt-reinforcement members 730 are spaced apart from each other in approximately equal increments around the circumference of the inner frame 104. However, it is not required that a skirt-reinforcement member 730 be utilized on skirt material of every side opening 118 of the row of side openings 118 around the circumference of the inner frame 104. Rather, a skirt-reinforcement member 730 may be utilized only on the side openings 118 having skirt material that may contact one or more leaflets 109 when the leaflets are opening and closing in situ. For example, the embodiment of FIG. 13 depicts an embodiment in which the transcatheter valve prosthesis 100 includes a total of three skirt-reinforcement members 1330 that are spaced apart from each other in approximately equal increments around the circumference of the inner frame 104. The skirt-reinforcement members 1330 are only on the side openings 118 having skirt material that may likely come into contact with leaflets 109 when the leaflets are opening and closing in situ. In another embodiment hereof depicted in FIG. 12, the transcatheter valve prosthesis 100 includes a total of eighteen skirt-reinforcement members 1230 such that a skirt-reinforcement member 1230 is directly attached to skirt material of each side opening 118 of the inner frame 104. At least one side opening 118 must include a skirt-reinforcement member 730 according to an aspect of the present disclosure.

The second end 734 of the skirt-reinforcement member 730 is directly attached to the inner skirt 112 via any suitable attachment mechanism, including but not limited to suture, adhesive, or welding. In an embodiment, the first end 732 of the skirt-reinforcement member 730 is directly attached to the outer frame 106 via any suitable attachment mechanism, including but not limited to suture, adhesive, or welding.

In another embodiment, an outer skirt (not shown) is coupled to a surface of the outer frame 106 and the first end 732 of the skirt-reinforcement member 730 is directly attached to the outer skirt. The outer skirt may be coupled to an inner or outer surface of the outer frame 106, and may be formed of a natural or biological material such as pericardium or another membranous tissue such as intestinal submucosa. Alternatively, the outer skirt may be a low-porosity woven fabric, such as polyester, Dacron fabric, or PTFE. In one embodiment, the outer skirt may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Figure 11:
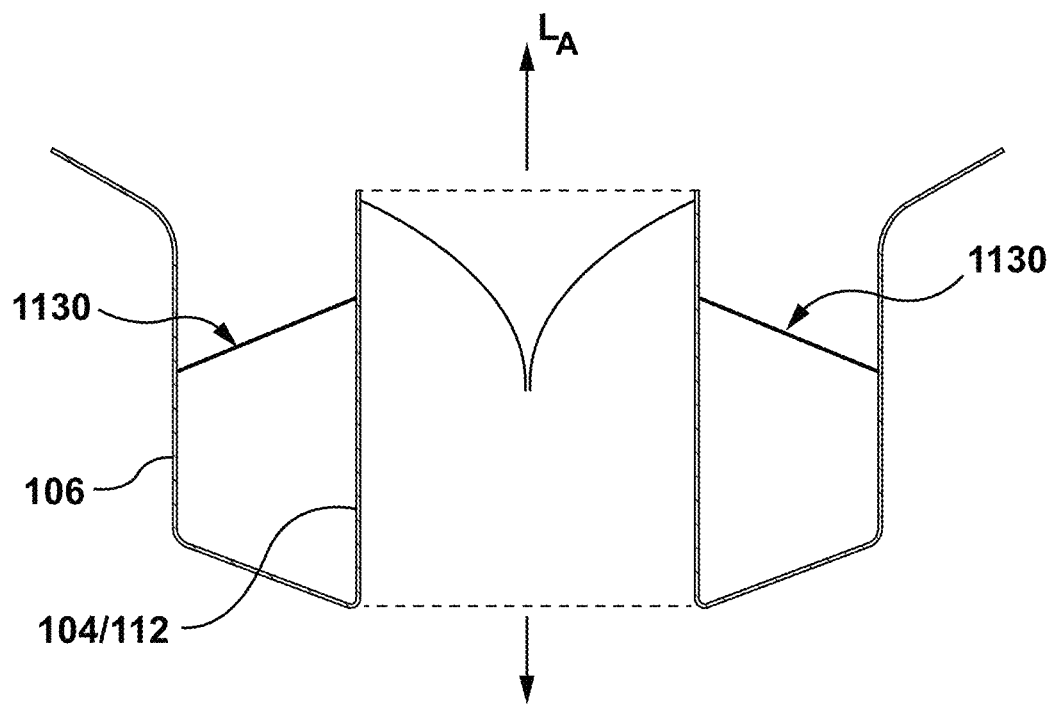
FIG. 11 is a cross-sectional view according to another embodiment hereof, wherein the transcatheter valve prosthesis is in its radially expanded configuration and wherein the transcatheter valve prosthesis further includes a plurality of skirt-reinforcement members in accordance with an aspect of the disclosure.

Notably, the length L of each skirt-reinforcement member 730 is configured such that the skirt-reinforcement member 730 is under tension when the transcatheter valve prosthesis 100 is in the radially expanded configuration. As best shown on FIG. 10, the skirt-reinforcement members 730 may have a generally linear or straight configuration between the inner frame 104 and the outer frame 106. Stated another way, the skirt-reinforcement members 730 may be oriented transverse with respect to the longitudinal axis LA of the transcatheter valve prosthesis 100. In another embodiment, which is depicted in FIG. 11, a first end 1132 of each skirt-reinforcement member 1130 is axially offset from a second end 1134 of the skirt-reinforcement member 1130. Stated another way, the skirt-reinforcement members 1130 may be oriented at an angle or a diagonal with respect to the longitudinal axis LA of the transcatheter valve prosthesis 100. Regardless of the orientation of the skirt-reinforcement members, the skirt-reinforcement members are configured to have sufficient tension along its length L when the transcatheter valve prosthesis 100 is in the expanded configuration to minimize radial movement of the inner skirt 112 throughout the cardiac cycle. As shown on FIG. 8B, the skirt-reinforcement members 730 are formed from a sufficiently flexible material so as to collapse, bunch, fold, or otherwise slacken when the transcatheter valve prosthesis 100 is in its radially compressed configuration.

Figure 17:
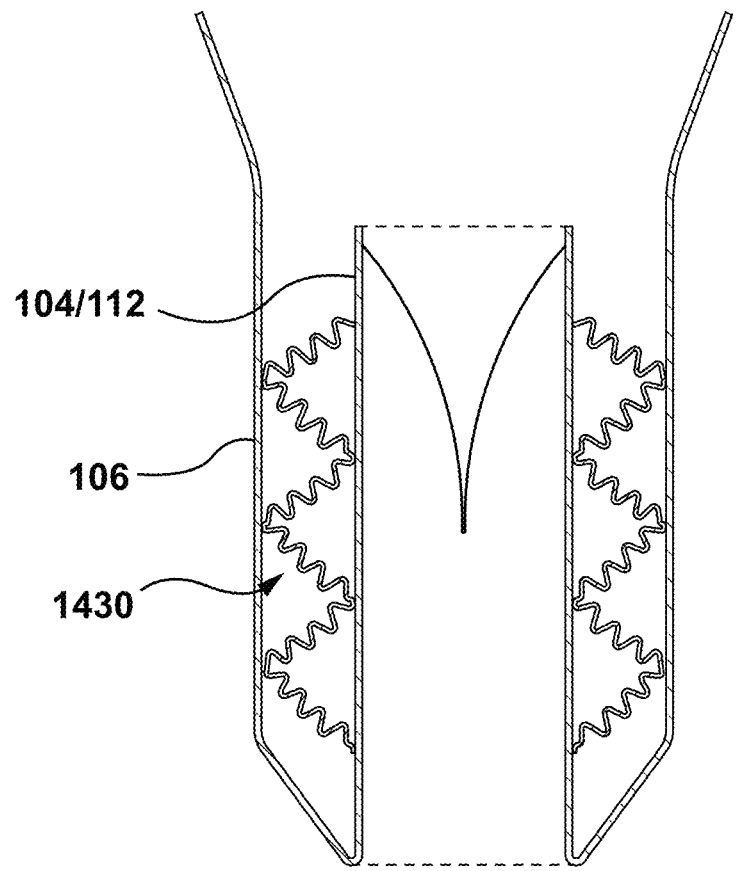
FIG. 17 is a cross-sectional view of FIG. 14, wherein the transcatheter valve prosthesis is in its radially compressed configuration.

Turning now to FIGS. 14-17, a skirt-reinforcement member 1430 according to another aspect of the disclosure is illustrated. FIG. 14 is a simplified cross-sectional view of the transcatheter valve prosthesis 100 in its radially expanded configuration, and the transcatheter valve prosthesis 100 further includes a skirt-reinforcement member 1430. FIG. 15 is a side view of the tubular skirt-reinforcement member 1430 removed from the transcatheter valve prosthesis 100 for sake of illustration only. FIG. 16 is a simplified illustration of a top view of FIG. 14, with the tubular skirt-reinforcement member 1430 being shown in phantom to depict placement thereof for sake of illustration only. FIG. 17 is a cross-sectional view of FIG. 14 with transcatheter valve prosthesis 100 is in its radially compressed configuration.

The skirt-reinforcement member 1430 is a flexible tubular or cylindrical component that is disposed between the outer frame 106 and the inner skirt 112. More particularly, the skirt-reinforcement member 1430 includes a tubular sleeve or body 1440 that defines a lumen 1446 therethrough. The tubular body 1440 has a first end 1442, a second end 1444, and a length L between the first end 1442 and the second end 1444. The length L of the tubular body 1440 is equal to or less than a length of the inner frame 104. The embodiment of FIGS. 14-17 depict that the length L is less the length of the inner frame 104. The tubular body 1440 has an inner surface 1447. When assembled onto the transcatheter valve prosthesis 100, the skirt-reinforcement member 1430 encircles or surrounds the inner frame 104 such that the inner surface 1447 is disposed adjacent to the outer surface of the inner frame 104, as best shown in the top view of FIG. 16. Stated another way, the lumen 1446 of the tubular body 1440 is aligned with the central lumen 110 of the inner frame 104. Suitable flexible materials for the tubular body 1440 include but are not limited to a low-porosity woven fabric, such as polyester, Dacron fabric, or PTFE. Further, the tubular body 1440 may be a knit or woven polyester, such as a polyester or PTFE knit, both of which can stretch and apply tension to the inner skirt 112.

The tubular body 1440 includes a series of alternating pleats 1449 defining circumferential out-folds 1448 and circumferential in-folds 1450 along the length L of the tubular body 1440. Each pleat 1449 extends or is oriented in a radial direction, and extends between a circumferential out-fold 1448 and an adjacent circumferential in-fold 1450. Along the length of the tubular body 1440, the circumferential in-folds 1450 and circumferential out-folds 1448 alternate such that a circumferential out-fold 1448 is disposed between a pair of adjacent circumferential in-folds 1450. The skirt-reinforcement member 1430 is attached to both the inner skirt 112 and the outer frame 106 so that the skirt-reinforcement member 1430 is configured to restrict or prevent billowing, or radial motion, of one or more unsupported portions of the inner skirt 112. Particularly, the circumferential out-folds 1448 of the skirt-reinforcement member 1430 are coupled to the outer frame 106 at one or more outer connection points and the circumferential in-folds 1450 of the skirt-reinforcement member 1430 is directly attached to the inner skirt 112 along unsupported portions of the inner skirt 112 at one or more inner connection points. Each inner connection point is along an unsupported portion of the inner skirt 112 that spans one or more of the plurality of side openings 118 of the inner frame 104. Since the circumferential out-folds 1448 are coupled to the outer frame 106, the skirt-reinforcement member 1430 applies tension to the inner skirt 112 and thereby prevents undesired billowing of the skirt material. The skirt-reinforcement member 1430 is formed from a flexible material such that it is configured to slacken when the transcatheter valve prosthesis 100 is in its radially compressed configuration, but is configured to under tension when the transcatheter valve prosthesis 100 is in its radially expanded configuration, thereby mitigating movement of the inner skirt 112 throughout the cardiac cycle.

The pleats 1449 of the tubular body 1440 each have a width that is configured such that the skirt-reinforcement member 1430 is under tension when the transcatheter valve prosthesis 100 is in the radially expanded configuration. More particularly, as shown on FIG. 14, each pleat 1449 has a width W from its circumferential in-fold 1450 to its circumferential out-fold 1448. Notably, the width W is configured such that the pleats 1449 of the skirt-reinforcement member 1430 are under tension when the transcatheter valve prosthesis 100 is in the radially expanded configuration. Stated another way, each pleat 1449 of the skirt-reinforcement member 1430 is configured to have sufficient tension along its width W when the transcatheter valve prosthesis 100 is in the expanded configuration to minimize radial movement of the inner skirt 112 throughout the cardiac cycle. As shown on FIG. 17, the skirt-reinforcement member 1430 is formed from a sufficiently flexible material so that the pleats 1449 are configured to collapse, bunch, fold, or otherwise slacken when the transcatheter valve prosthesis 100 is in its radially compressed configuration.

The number and placement of the outer and inner connection points may vary according to application. In an embodiment, the outer connection points are longitudinally spaced apart from each other and are also circumferentially spaced apart from each other. The number of outer connection points is selected such that the skirt-reinforcement member 1430 is configured to have sufficient tension along its width W when the transcatheter valve prosthesis 100 is in the expanded configuration to minimize radial movement of the inner skirt 112 throughout the cardiac cycle. The inner connection points are longitudinally spaced apart from each other and are also circumferentially spaced apart from each other. Each inner connection point is along an unsupported portion of the inner skirt 112 that spans one or more of the plurality of side openings 118 of the inner frame 104, and thus the number of inner connection points is selected depending upon how many unsupported portions of the inner skirt 112 require reinforcement. In an embodiment, an inner connection point is disposed at each side opening 118 of the row of side openings 118 around the circumference of the inner frame 104. However, in another embodiment, inner connection points are utilized only on the side openings 118 having skirt material that may come into contact with leaflets 109 when the leaflets are opening and closing in situ.

At the inner connection points, the circumferential in-folds 1450 of the skirt-reinforcement member 1430 are directly attached to the inner skirt 112 via any suitable attachment mechanism, including but not limited to suture, adhesive, or welding. In an embodiment, at the outer connection points, the circumferential out-folds 1448 of the skirt-reinforcement member 1430 are directly attached to the outer frame 106 via any suitable attachment mechanism, including but not limited to suture, adhesive, or welding. In another embodiment, an outer skirt (not shown) is coupled to a surface of the outer frame 106 and at the outer connection points, the circumferential out-folds 1448 of the skirt-reinforcement member 1430 are directly attached to the outer skirt. The outer skirt may be coupled to an inner or outer surface of the outer frame 106, and may be formed of a natural or biological material such as pericardium or another membranous tissue such as intestinal submucosa. Alternatively, the outer skirt may be a low-porosity woven fabric, such as polyester, Dacron fabric, or PTFE. In one embodiment, the outer skirt may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Figure 18:
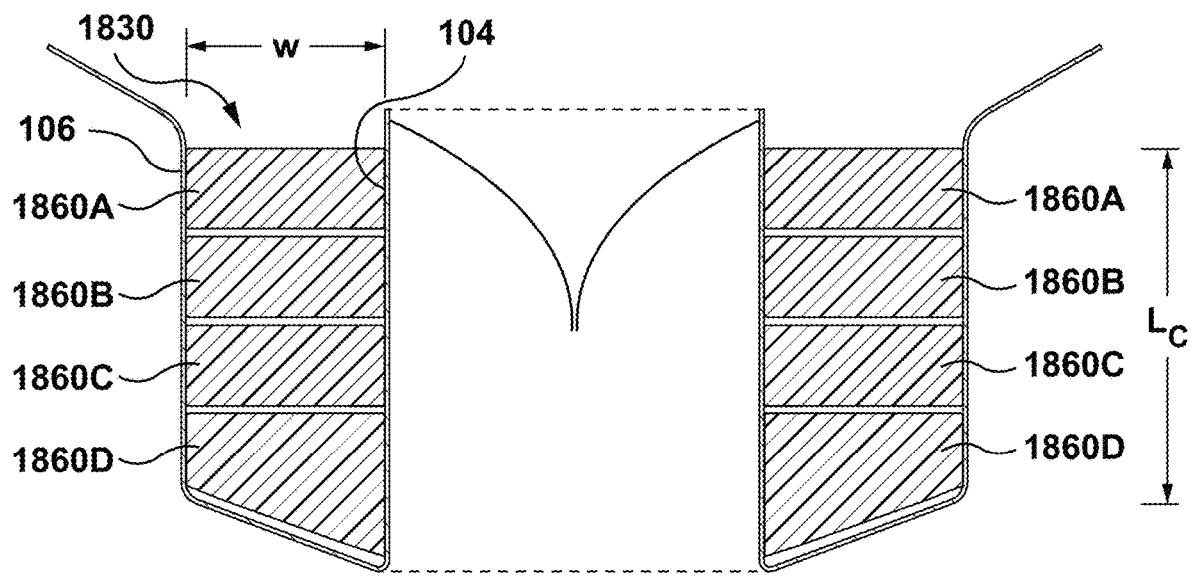
FIG. 18 is a cross-sectional view according to another embodiment hereof, wherein the transcatheter valve prosthesis is in its radially expanded configuration and wherein the transcatheter valve prosthesis further includes a plurality of toroidal components in accordance with an aspect of the disclosure.
Figure 20:
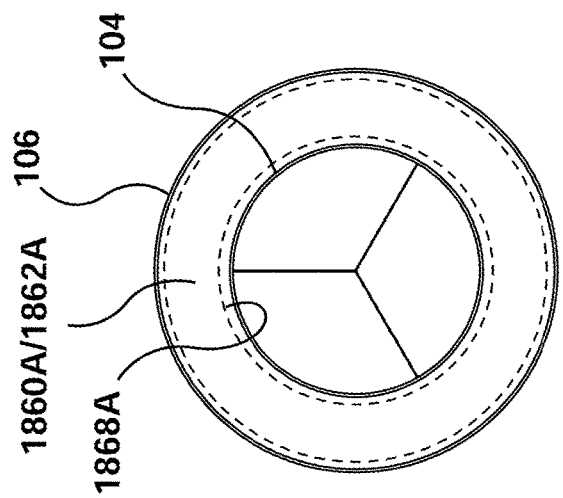
FIG. 20 is a simplified illustration of a top view of FIG. 18, with the toroidal components being shown in phantom to depict placement thereof for sake of illustration only.
Figure 19:
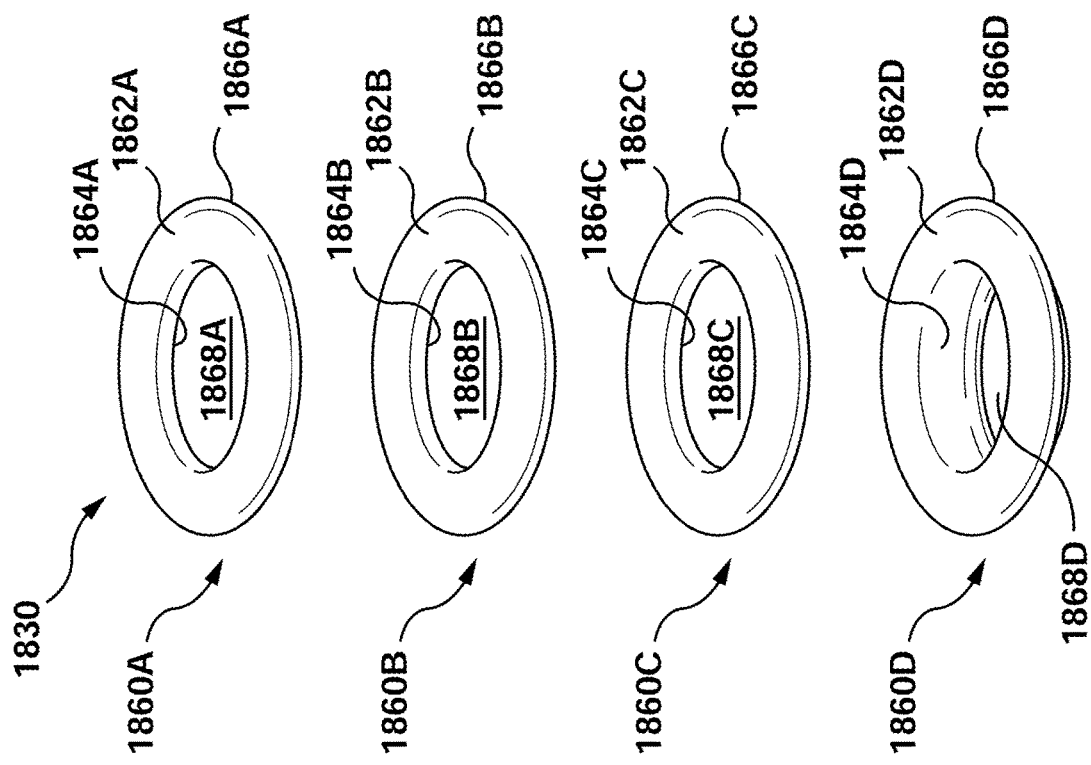
FIG. 19 is a perspective view of the plurality of toroidal components of FIG. 18, wherein the toroidal components are removed from the transcatheter valve prosthesis for sake of illustration only.
Figure 21:
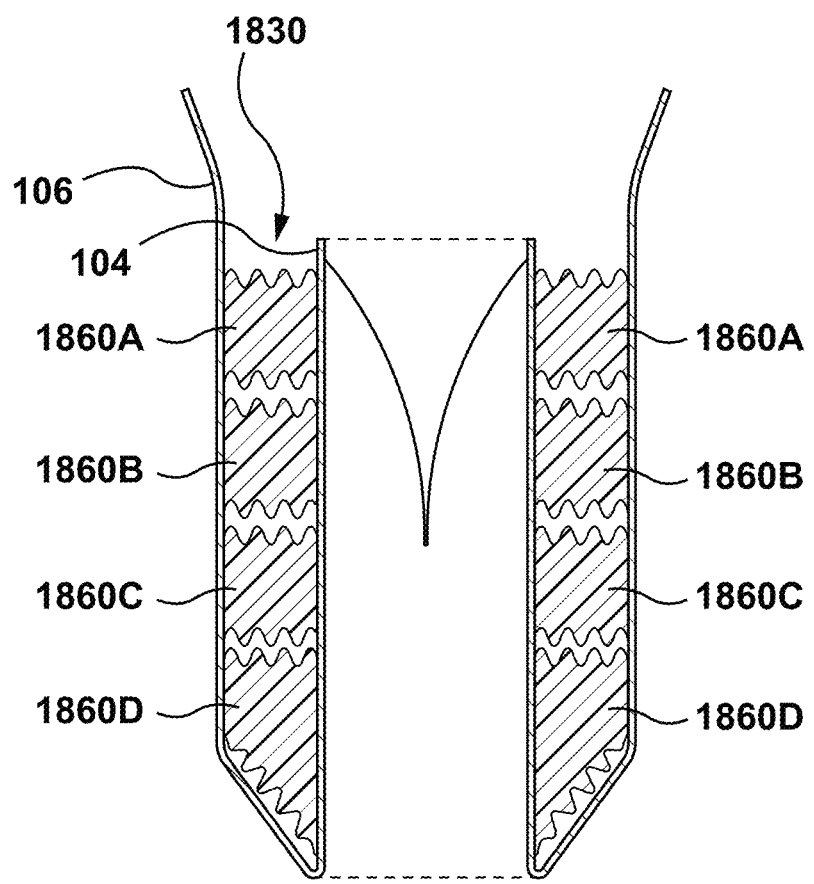
FIG. 21 is a cross-sectional view of FIG. 18, wherein the transcatheter valve prosthesis is in its radially compressed configuration.

Turning now to FIGS. 18-21, another aspect of the disclosure is illustrated. FIG. 18 is a simplified cross-sectional view of the transcatheter valve prosthesis 100 in its radially expanded configuration, and the transcatheter valve prosthesis 100 further includes a plurality of toroidal components 1860A, 1860B, 1860C, 1860D. FIG. 19 is a side view of the plurality of toroidal components 1860A, 1860B, 1860C, 1860D removed from the transcatheter valve prosthesis 100 for sake of illustration only. FIG. 20 is a simplified illustration of a top view of FIG. 18, with the plurality of toroidal components 1860A, 1860B, 1860C, 1860D being shown in phantom to depict placement thereof for sake of illustration only. FIG. 21 is a cross-sectional view of FIG. 18 with transcatheter valve prosthesis 100 is in its radially compressed configuration.

A skirt replacement assembly 1858 includes the plurality of toroidal components 1860A, 1860B, 1860C, 1860D. Rather than having an inner skirt coupled to the inner frame 104, and an outer skirt component coupled to the outer frame 106, the plurality of toroidal components 1860A, 1860B, 1860C, 1860D of the skirt replacement assembly 1858 function as the skirt components for the dual frame 102. Stated another way, as compared to certain embodiments disclosed above in which the inner skirt 112 is coupled to the inner frame 104 and an outer skirt component may be coupled to the outer frame 106, all skirt components are replaced by a series or plurality of toroidal components 1860A, 1860B, 1860C, 1860D disposed between the outer frame 106 and the inner frame 106. In the embodiment of FIGS. 18-21, the skirt replacement assembly 1858 includes a total of four toroidal components 1860A, 1860B, 1860C, 1860D. However, a greater or lesser number of toroidal components may be utilized. When assembled onto the dual frame 102, the toroidal components 1860A, 1860B, 1860C, 1860D abut against and contact each other in an axial or longitudinal direction and have a collective length $L_C$. The collective length $L_C$ of the plurality of toroidal components 1860A, 1860B, 1860C, 1860D is substantially the same as a length of the inner frame 104. Stated another way, the plurality of toroidal components 1860A, 1860B, 1860C, 1860D collectively extend an entire length of the inner frame 104.

Each toroidal component 1860A, 1860B, 1860C, 1860D of the plurality of toroidal components has a toroidal or doughnut-shaped body 1862A, 1862B, 1862C, 1862D that defines a lumen 1866A, 1866B, 1866C, 1866D therethrough. Each toroidal body 1862A, 1862B, 1862C, 1862D has an inner circumferential surface 1864A, 1864B, 1864C, 1864D and an outer circumferential surface 1866A, 1866B, 1866C, 1866D. When assembled onto the transcatheter valve prosthesis 100, each toroidal component 1860A, 1860B, 1860C, 1860D encircles or surrounds the inner frame 104 such that the inner circumferential surface 1864A, 1864B, 1864C, 1864D is disposed adjacent to the outer surface of the inner frame 104, as best shown in the top view of FIG. 20. Stated another way, the inner circumferential surface 1864A, 1864B, 1864C, 1864D of each toroidal body 1862A, 1862B, 1862C, 1862D is aligned with the central lumen 110 of the inner frame 104. As described in more detail herein, the toroidal bodies 1862A, 1862B, 1862C, 1862D are formed from a flexible material such that they are configured to slacken when the transcatheter valve prosthesis 100 is in its radially compressed configuration, but are configured to be under tension when the transcatheter valve prosthesis 100 is in its radially expanded configuration, thereby mitigating movement of the unsupported portions of the inner circumferential surface 1864A, 1864B, 1864C, 1864D throughout the cardiac cycle. Suitable flexible materials for the toroidal components 1860A, 1860B, 1860C, 1860D include but are not limited to a low-porosity woven fabric, such as polyester, Dacron fabric, or PTFE. Further, the toroidal components 1860A, 1860B, 1860C, 1860D may be a knit or woven polyester, such as a polyester or PTFE knit, both of which can be under tension and slacken when tension is released.

The outer circumferential surface 1866A, 1866B, 1866C, 1866D of each toroidal component 1860A, 1860B, 1860C, 1860D is directly attached to the outer frame 106 via any suitable attachment mechanism, including but not limited to suture, adhesive, or welding. The inner circumferential surface 1864A, 1864B, 1864C, 1864D of each toroidal component 1860A, 1860B, 1860C, 1860D is directly attached to the inner frame 104 via any suitable attachment mechanism, including but not limited to suture, adhesive, or welding. The outer circumferential surfaces 1866A, 1866B, 1866C, 1866D collectively form or function as an impermeable, continuous skirt on the outer frame 106 and the inner circumferential surfaces 1864A, 1864B, 1864C, 1864D collectively form or function as impermeable, continuous skirt on the inner frame 104.

The toroidal components 1860A, 1860B, 1860C, 1860D are attached to both the inner frame 104 and the outer frame 106, and the toroidal bodies 1862A, 1862B, 1862C, 1862D that extend between the inner frame 104 and the outer frame 106 are configured to be under tension when the transcatheter valve prosthesis 100 is in the expanded configuration. Each toroidal component 1860A, 1860B, 1860C, 1860D has a width W between its outer circumferential surface 1866A, 1866B, 1866C, 1866D and its inner circumferential surface 1864A, 1864B, 1864C, 1864D. The width W is configured such that each toroidal component 1860A, 1860B, 1860C, 1860D is under tension when the transcatheter valve prosthesis 100 is in the radially expanded configuration. Thus, when the toroidal bodies 1862A, 1862B, 1862C, 1862D are under tension, billowing, or radial motion, of the unsupported portions of the inner circumferential surface 1864A, 1864B, 1864C, 1864D is prevented or restricted. As shown on FIG. 21, each toroidal component 1860A, 1860B, 1860C, 1860D is formed from a sufficiently flexible material so that it is configured to collapse, fold, or otherwise slacken when the transcatheter valve prosthesis 100 is in its radially compressed configuration.

The skirt-reinforcement members 730, 1130, 1230, 1330, 1430 may be utilized on any transcatheter heart valve prosthesis that includes a skirt on a portion thereof. For example, alternative implant anchors or outer frames can be utilized to apply tension to the skirt material to prevent billowing. The skirt-reinforcement members 730, 1130, 1230, 1330, 1430 serve to limit the radial motion or billowing of the skirt material of the inner skirt, thereby minimizing risk of damage to both the skirt and the leaflets. Depending on the configuration of the frame, the particular placement of the skirt-reinforcement members may vary. In an embodiment, the skirt-reinforcement members are positioned downstream of a margin of attachment (MOA) of the leaflets of the transcatheter heart valve prosthesis and are positioned over a side opening of the frame that includes skirt material over a portion thereof. The configuration of the frames and the configuration of the side openings of the frames is non-limiting and may vary, as exemplified in the following figures.

Figure 22:
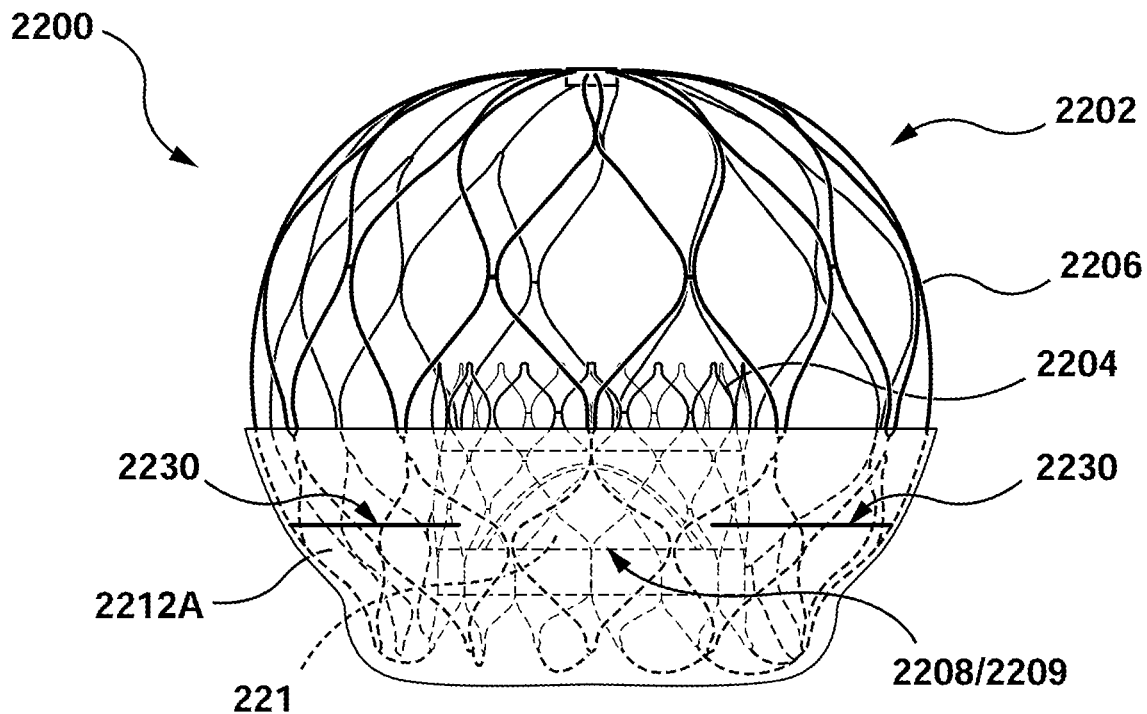
FIG. 22 is a perspective view of a transcatheter valve prosthesis according to another embodiment hereof, wherein the transcatheter valve prosthesis is in its radially expanded configuration and wherein the transcatheter valve prosthesis further includes a plurality of skirt-reinforcement members in accordance with an aspect of the disclosure.

FIG. 22 depicts a perspective view of a transcatheter heart valve prosthesis 2200 in accordance with another aspect of the disclosure. The transcatheter valve prosthesis 2200 includes a stent or dual frame 2202 and a prosthetic valve component 2208 including at least one leaflet 2209 disposed within and secured to the dual frame 2202. The dual frame 2202 includes a valve support or inner frame 2204 at least partially surrounded by and coupled to an anchor element or outer frame 2206. The inner frame 2204 is a tubular stent structure that is configured to support the prosthetic valve component 2208 therein. In an embodiment, the inner frame 2204 has a substantially cylindrical shape and the outer frame 2206 has a substantially spherical or bulbous shape.

The inner frame 2204 includes a skirt 2212 coupled to a surface thereof. The skirt 2212 may be formed from the same materials described above with respect to the skirt 112. The prosthetic valve component 2208 of the transcatheter heart valve prosthesis 2200 is capable of regulating flow therethrough via valve leaflets that may form a replacement valve. As described above with respect to the prosthetic valve component 108, when deployed in situ, the prosthetic valve component 2208 in a closed state is configured to block blood flow in one direction to regulate blood flow through a central lumen of the frame 2202.

The valve leaflets 2209 may be attached to the skirt 2212. The skirt 2212 may billow during valve opening and closing in situ, and the leaflets 2209 may contact the skirt 2212. Such billowing may undesirably result in contact between the skirt 2212 and the leaflets 2209 of the transcatheter heart valve prosthesis 2200. If the leaflets 2209 of the transcatheter heart valve prosthesis 2200 contact the skirt 2212 during opening and closing, such contact may cause early leaflet tissue abrasion as well as early skirt abrasion. Additionally, the greater relative motion between the skirt 2212 and the valve support 2204 may further induce early skirt abrasion. Thus, the transcatheter heart valve prosthesis 2200 further includes a plurality of skirt-reinforcement members 2230.

As described above with respect to the skirt-reinforcement members 730 described above, the skirt-reinforcement members 2230 reinforce the material of the skirt 2212 that spans across the side openings of the inner frame 2204 to limit the radial motion or billowing of the skirt material, thereby minimizing risk of damage to both the skirt 2212 and the leaflets 2209.

Each skirt-reinforcement member 2230 is a flexible tether that spans or extends between the outer frame 2206 and the inner skirt 2212. Each skirt-reinforcement member 2230 may be formed from the same materials described above with respect to the skirt-reinforcement members 730. Each skirt-reinforcement member 2230 is configured to restrict or prevent billowing, or radial motion, of an unsupported portion of the inner skirt 2212 that spans across or extends over a side opening of the inner frame 2204. Each skirt-reinforcement member 2230 has a first end coupled to the outer frame 2206 and a second end directly attached to the inner skirt 2212 along the unsupported portion of the inner skirt 2212 that spans one or more of the plurality of side openings of the inner frame 2204. Since the first end of the skirt-reinforcement member 2230 is coupled to the outer frame 2206, the skirt-reinforcement member 2230 applies tension to the inner skirt 2212 and thereby prevents undesired billowing of the skirt material. The skirt-reinforcement member 2230 is formed from a flexible material such that it is configured to slacken when the transcatheter valve prosthesis 2200 is in its radially compressed configuration, but is configured to be under tension when the transcatheter valve prosthesis 2200 is in its radially expanded configuration, thereby mitigating movement of the inner skirt 2212 throughout the cardiac cycle.

The second end of the skirt-reinforcement member 2230 is directly attached to the inner skirt 2212 via any suitable attachment mechanism described herein with respect to the skirt-reinforcement members 730. In an embodiment, the first end of the skirt-reinforcement member 2230 is directly attached to the outer frame 2206 via any suitable attachment mechanism described herein with respect to the skirt-reinforcement members 730. In another embodiment, an outer skirt 2212A is coupled to a surface of the outer frame 2206 and the first end of the skirt-reinforcement member 2230 is directly attached to the outer skirt.

In the embodiment of FIG. 22, the plurality of skirt-reinforcement members 2230 are spaced apart from each other in approximately equal increments around the circumference of the inner frame 2204 and a skirt-reinforcement member 2230 is utilized only on the side openings having skirt material that may come into contact with leaflets 2209 when the leaflets are opening and closing in situ. At least one side opening must include a skirt-reinforcement member 2230 according to an aspect of the present disclosure.

Notably, the length of each skirt-reinforcement member 2230 is configured such that the skirt-reinforcement member 2230 is under tension when the transcatheter valve prosthesis 2200 is in the radially expanded configuration. The skirt-reinforcement members 2230 may have a generally linear or straight configuration between the inner frame 2204 and the outer frame 2206. Stated another way, the skirt-reinforcement members 2230 may be oriented transverse with respect to a longitudinal axis of the transcatheter valve prosthesis 2200. In another embodiment (not shown), the first end of each skirt-reinforcement member 2230 is axially offset from the second end of the skirt-reinforcement member 2230. Stated another way, the skirt-reinforcement members 2230 may be oriented at an angle or a diagonal with respect to the longitudinal axis of the transcatheter valve prosthesis 2200. Regardless of the orientation of the skirt-reinforcement members, the skirt-reinforcement members are configured to have sufficient tension along its length when the transcatheter valve prosthesis 2200 is in the expanded configuration to minimize radial movement of the inner skirt 2212 throughout the cardiac cycle. The skirt-reinforcement members 2230 are formed from a sufficiently flexible material so as to collapse, bunch, fold, or otherwise slacken when the transcatheter valve prosthesis 2200 is in its radially compressed configuration.

Although the transcatheter valve prosthesis 2200 is depicted with skirt-reinforcement members 2230 that are similar to skirt-reinforcement members 730, the transcatheter valve prosthesis 2200 may incorporate a skirt-reinforcement member that is similar to the skirt-reinforcement member 1430 or may incorporate a skirt replacement assembly that is similar to the skirt replacement assembly 1858. For example, as alternative to the plurality of skirt-reinforcement members 2230, the transcatheter heart valve prosthesis 2200 may include a flexible tubular or cylindrical component that is disposed between the outer frame 2206 and the inner skirt 2212. The cylindrical component would be attached to the skirt 2212 and would be the same as the skirt-reinforcement member 1430 described above. As another example, as alternative to the plurality of skirt-reinforcement members 2230, the transcatheter heart valve prosthesis 2200 may include a skirt replacement assembly includes the plurality of toroidal components. Rather than having an inner skirt coupled to the inner frame 2204, and an outer skirt component coupled to the outer frame 2206, the plurality of toroidal components of the skirt replacement assembly function as the skirt components for the dual frame 2202 in the same manner as the skirt replacement assembly 1858 described above.

Figure 23:
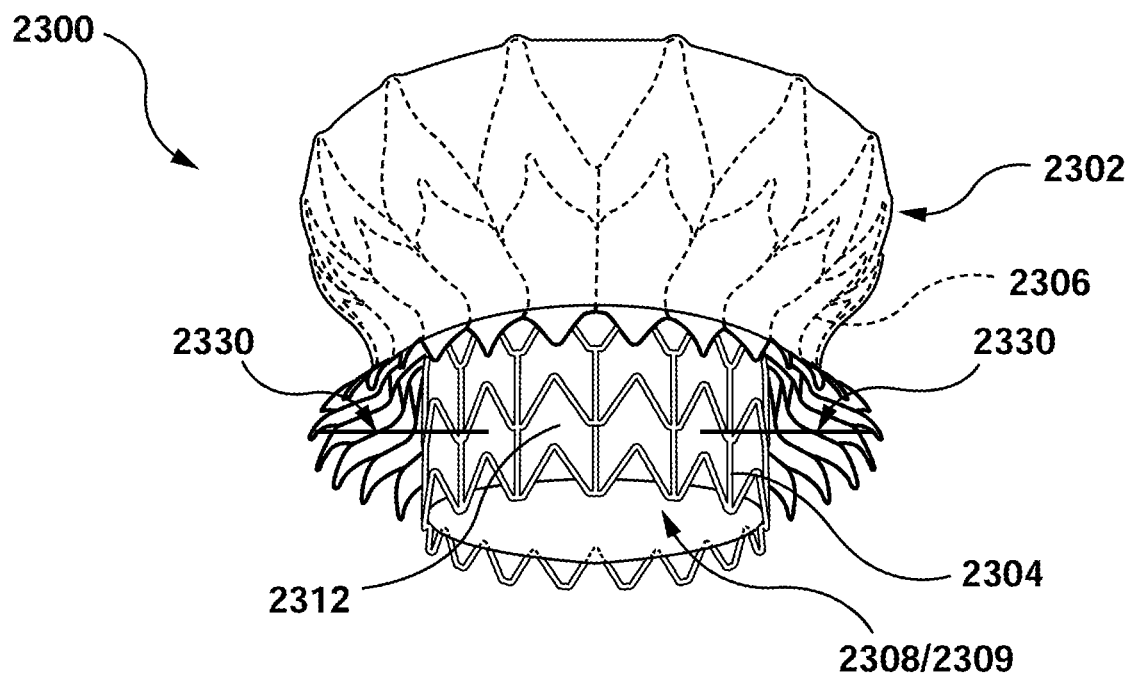
FIG. 23 is a perspective view of a transcatheter valve prosthesis according to another embodiment hereof, wherein the transcatheter valve prosthesis is in its radially expanded configuration and wherein the transcatheter valve prosthesis further includes a plurality of skirt-reinforcement members in accordance with an aspect of the disclosure.

FIG. 23 depicts a perspective view of a transcatheter heart valve prosthesis 2300 in accordance with another aspect of the disclosure. The transcatheter valve prosthesis 2300 includes a stent or dual frame 2302 and a prosthetic valve component 2308 including at least one leaflet 2309 disposed within and secured to the dual frame 2302. The dual frame 2302 includes a valve support or inner frame 2304 at least partially surrounded by and coupled to an anchor element or outer frame 2306. The inner frame 2304 is a tubular stent structure that is configured to support the prosthetic valve component 2308 therein. In an embodiment, the inner frame 2304 has a substantially cylindrical shape and the outer frame 2306 has a substantially hourglass shape.

The inner frame 2304 includes a skirt 2312 coupled to a surface thereof. The skirt 2312 may be formed from the same materials described above with respect to the skirt 112. The prosthetic valve component 2308 of the transcatheter heart valve prosthesis 2300 is capable of regulating flow therethrough via valve leaflets that may form a replacement valve. As described above with respect to the prosthetic valve component 108, when deployed in situ, the prosthetic valve component 2308 in a closed state is configured to block blood flow in one direction to regulate blood flow through a central lumen of the frame 2302.

The valve leaflets 2309 may be attached to the skirt 2312. The skirt 2312 may billow during valve opening and closing in situ, and the leaflets 2309 may contact the skirt 2312. Such billowing may undesirably result in contact between the skirt 2312 and the leaflets 2309 of the transcatheter heart valve prosthesis 2300. If the leaflets 2309 of the transcatheter heart valve prosthesis 2300 contact the skirt 2312 during opening and closing, such contact may cause early leaflet tissue abrasion as well as early skirt abrasion. Additionally, the greater relative motion between the skirt 2312 and the valve support 2304 may further induce early skirt abrasion. Thus, the transcatheter heart valve prosthesis 2300 further includes a plurality of skirt-reinforcement members 2330. As described above with respect to the skirt-reinforcement members 730 described above, the skirt-reinforcement members 2330 reinforce the material of the skirt 2312 that spans across the side openings of the inner frame 2304 to limit the radial motion or billowing of the skirt material, thereby minimizing risk of damage to both the skirt 2312 and the leaflets 2309.

Each skirt-reinforcement member 2330 is a flexible tether that spans or extends between the outer frame 2306 and the inner skirt 2312. Each skirt-reinforcement member 2330 may be formed from the same materials described above with respect to the skirt-reinforcement members 730. Each skirt-reinforcement member 2330 is configured to restrict or prevent billowing, or radial motion, of an unsupported portion of the inner skirt 2312 that spans across or extends over a side opening of the inner frame 2304. Each skirt-reinforcement member 2330 has a first end coupled to the outer frame 2306 and a second end directly attached to the inner skirt 2312 along the unsupported portion of the inner skirt 2312 that spans one or more of the plurality of side openings of the inner frame 2304. The first end of the skirt-reinforcement member 2330 is directly attached to the outer frame 2306 via any suitable attachment mechanism described herein with respect to the skirt-reinforcement members 730. The second end of the skirt-reinforcement member 2330 is directly attached to the inner skirt 2312 via any suitable attachment mechanism described herein with respect to the skirt-reinforcement members 730. Since the first end of the skirt-reinforcement member 2330 is coupled to the outer frame 2306, the skirt-reinforcement member 2330 applies tension to the inner skirt 2312 and thereby prevents undesired billowing of the skirt material. The skirt-reinforcement member 2330 is formed from a flexible material such that it is configured to slacken when the transcatheter valve prosthesis 2300 is in its radially compressed configuration, but is configured to be under tension when the transcatheter valve prosthesis 2300 is in its radially expanded configuration, thereby mitigating movement of the inner skirt 2312 throughout the cardiac cycle.

In the embodiment of FIG. 23, the plurality of skirt-reinforcement members 2330 are spaced apart from each other in approximately equal increments around the circumference of the inner frame 2304 and a skirt-reinforcement member 2330 is utilized only on the side openings having skirt material that may come into contact with leaflets 2309 when the leaflets are opening and closing in situ. At least one side opening must include a skirt-reinforcement member 2330 according to an aspect of the present disclosure.

Notably, the length of each skirt-reinforcement member 2330 is configured such that the skirt-reinforcement member 2330 is under tension when the transcatheter valve prosthesis 2300 is in the radially expanded configuration. The skirt-reinforcement members 2330 may have a generally linear or straight configuration between the inner frame 2304 and the outer frame 2306. Stated another way, the skirt-reinforcement members 2330 may be oriented transverse with respect to the longitudinal axis LA of the transcatheter valve prosthesis 2300. In another embodiment (not shown), the first end of each skirt-reinforcement member 2330 is axially offset from the second end of the skirt-reinforcement member 2330. Stated another way, the skirt-reinforcement members 2330 may be oriented at an angle or a diagonal with respect to the longitudinal axis LA of the transcatheter valve prosthesis 2300. Regardless of the orientation of the skirt-reinforcement members, the skirt-reinforcement members are configured to have sufficient tension along its length when the transcatheter valve prosthesis 2300 is in the expanded configuration to minimize radial movement of the inner skirt 2312 throughout the cardiac cycle. The skirt-reinforcement members 2330 are formed from a sufficiently flexible material so as to collapse, bunch, fold, or otherwise slacken when the transcatheter valve prosthesis 2300 is in its radially compressed configuration.

Although the transcatheter valve prosthesis 2300 is depicted with skirt-reinforcement members 2330 that are similar to skirt-reinforcement members 730, the transcatheter valve prosthesis 2300 may incorporate a skirt-reinforcement member that is similar to skirt-reinforcement member 1430 or may incorporate a skirt replacement assembly that is similar to the skirt replacement assembly 1858. For example, as alternative to the plurality of skirt-reinforcement members 2330, the transcatheter heart valve prosthesis 2300 may include a flexible tubular or cylindrical component that is disposed between the outer frame 2306 and the inner skirt 2312. The cylindrical component would be attached to the skirt 2312 and would be the same as the skirt-reinforcement member 1430 described above. As another example, as alternative to the plurality of skirt-reinforcement members 2330, the transcatheter heart valve prosthesis 2300 may include a skirt replacement assembly includes the plurality of toroidal components. Rather than having an inner skirt coupled to the inner frame 2304, and an outer skirt component coupled to the outer frame 2306, the plurality of toroidal components of the skirt replacement assembly function as the skirt components for the dual frame 2302 in the same manner as the skirt replacement assembly 1858 described above.

The above-described embodiments depict dual frame prostheses in which an outer frame is leveraged as an anchoring point for a tether or material connection to reinforce an inner skirt (attached to an inner frame) around the leaflets to mitigate billowing of the skirt material. The skirt-reinforcement members reinforce the material of a skirt that spans across the side opening of the inner frame of the valve prosthesis using connections between the material of the skirt and the outer frame of the valve prosthesis. However, the concepts described herein are not necessarily limited to dual frame prostheses. The skirt-reinforcement members described herein may be applied to several different types of anchoring points to mitigate billowing of the skirt material. For example, the skirt-reinforcement members may be attached to a tether anchoring component of the prosthesis to mitigate billowing of the skirt material. In another example, the skirt-reinforcement members may be attached to a docking or external sealing component configured to receive a valve prosthesis to mitigate billowing of the skirt material of the valve prosthesis.

Figure 24A:
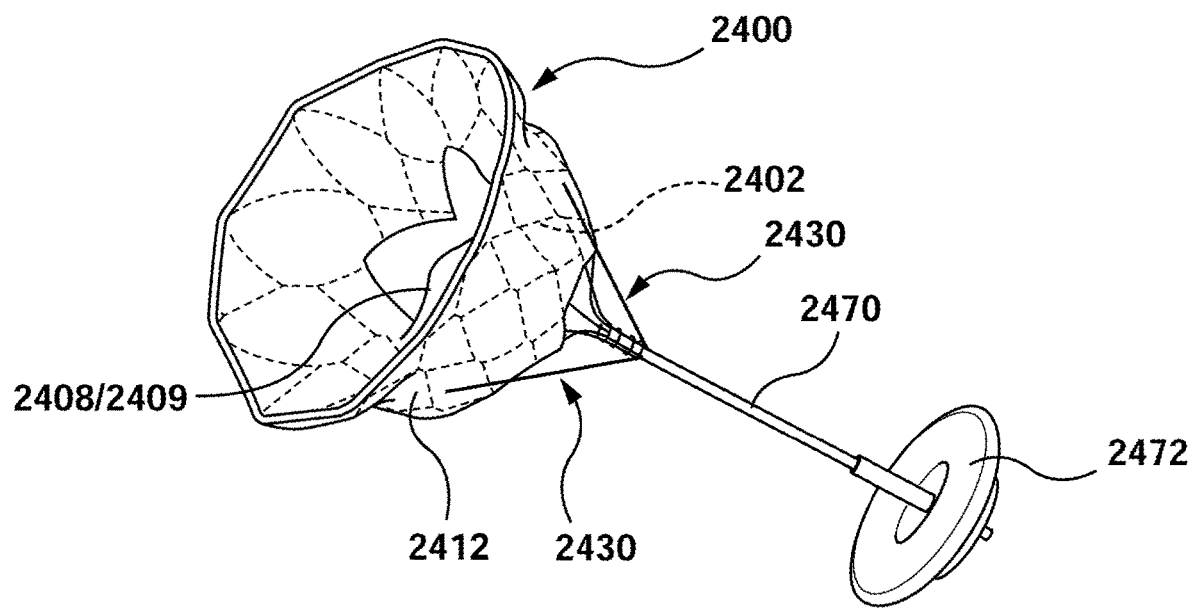
FIG. 24A is a perspective view of a transcatheter valve prosthesis according to another embodiment hereof, wherein the transcatheter valve prosthesis is in its radially expanded configuration and wherein the transcatheter valve prosthesis further includes a plurality of skirt-reinforcement members in accordance with an aspect of the disclosure.
Figure 24B:
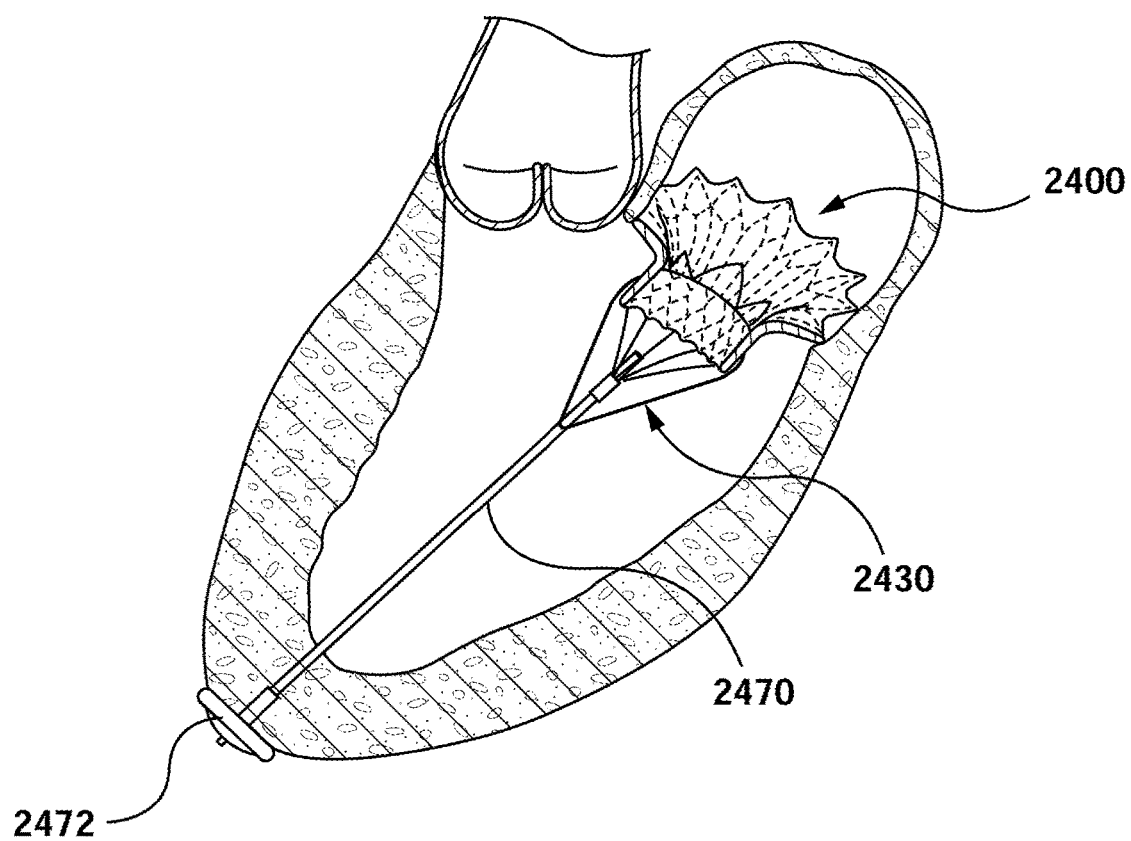
FIG. 24B is a perspective view of the transcatheter valve prosthesis of FIG. 24A in situ.

For example, FIGS. 24A and 24B depict perspective views of a transcatheter heart valve prosthesis 2400 in accordance with another aspect of the disclosure. The transcatheter valve prosthesis 2400 includes a stent 2402 and a prosthetic valve component 2408 including at least one leaflet 2409 disposed within and secured to the stent 2402. The stent 2402 is configured to support the prosthetic valve component 2408 therein. A tether 2470 extends between the stent 2402 and an anchor 2472. The anchor 2472 is configured to be disposed on an external surface of the heart. The stent 2402, tether 2470, and anchor 2472 are further described in U.S. Pat. No. 9,986,993 to Vidlund et al., herein incorporated by reference in its entirety.

The stent 2402 includes a skirt 2412 coupled to a surface thereof. The skirt 2412 may be formed from the same materials described above with respect to the skirt 112. The prosthetic valve component 2408 of the transcatheter heart valve prosthesis 2400 is capable of regulating flow therethrough via valve leaflets that may form a replacement valve. As described above with respect to the prosthetic valve component 108, when deployed in situ, the prosthetic valve component 2408 in a closed state is configured to block blood flow in one direction to regulate blood flow through a central lumen of the stent 2402.

The valve leaflets 2409 may be attached to the skirt 2412. The skirt 2412 may billow during valve opening and closing in situ, and the leaflets 2409 may contact the skirt 2412. Such billowing may undesirably result in contact between the skirt 2412 and the leaflets 2409 of the transcatheter heart valve prosthesis 2400. If the leaflets 2409 of the transcatheter heart valve prosthesis 2400 contact the skirt 2412 during opening and closing, such contact may cause early leaflet tissue abrasion as well as early skirt abrasion. Additionally, the greater relative motion between the skirt 2412 and the valve support 2404 may further induce early skirt abrasion. Thus, the transcatheter heart valve prosthesis 2400 further includes a plurality of skirt-reinforcement members 2430. As described above with respect to the skirt-reinforcement members 730 described above, the skirt-reinforcement members 2430 reinforce the material of the skirt 2412 that spans across the side openings of the frame 2402 to limit the radial motion or billowing of the skirt material, thereby minimizing risk of damage to both the skirt 2412 and the leaflets 2409.

Each skirt-reinforcement member 2430 is a flexible tether that spans or extends between the skirt 2412 and the tether 2470. Each skirt-reinforcement member 2430 may be formed from the same materials described above with respect to the skirt-reinforcement members 730. Each skirt-reinforcement member 2430 is configured to restrict or prevent billowing, or radial motion, of an unsupported portion of the skirt 2412 that spans across or extends over a side opening of the stent 2402. Each skirt-reinforcement member 2430 has a first end attached to a midportion of the tether 2470 and a second end directly attached to the skirt 2412 along the unsupported portion of the skirt 2412 that spans one or more of the plurality of side openings of the stent 2402. The first end of the skirt-reinforcement member 2430 is directly attached to the tether 2470 via adhesive or welding. The second end of the skirt-reinforcement member 2430 is directly attached to the skirt 2412 via any suitable attachment mechanism described herein with respect to the skirt-reinforcement members 730. Since the first end of the skirt-reinforcement member 2430 is coupled to the tether 2470, the skirt-reinforcement member 2430 applies tension to the skirt 2412 and thereby prevents undesired billowing of the skirt material. The skirt-reinforcement member 2430 is formed from a flexible material such that it is configured to slacken when the transcatheter valve prosthesis 2400 is in its radially compressed configuration, but is configured to be under tension when the transcatheter valve prosthesis 2400 is in its radially expanded configuration, thereby mitigating movement of the skirt 2412 throughout the cardiac cycle.

In the embodiment of FIG. 24, the plurality of skirt-reinforcement members 2430 are spaced apart from each other in approximately equal increments around the circumference of the stent 2402 and a skirt-reinforcement member 2430 is utilized only on the side openings having skirt material that may come into contact with leaflets 2409 when the leaflets are opening and closing in situ. At least one side opening must include a skirt-reinforcement member 2430 according to an aspect of the present disclosure.

Notably, the length of each skirt-reinforcement member 2430 is configured such that the skirt-reinforcement member 2430 is under tension when the transcatheter valve prosthesis 2400 is in the radially expanded configuration. The skirt-reinforcement members are configured to have sufficient tension along its length when the transcatheter valve prosthesis 2400 is in the expanded configuration to minimize radial movement of the skirt 2412 throughout the cardiac cycle.

Figures 25, 26:
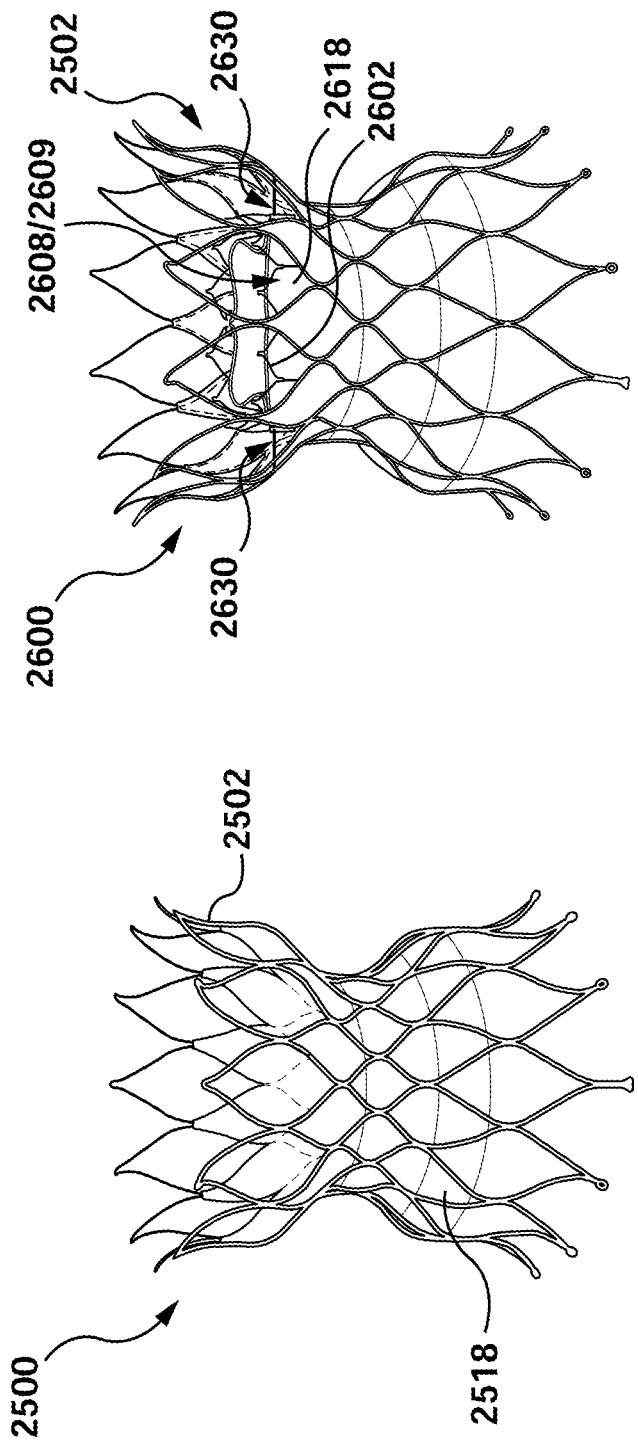
FIG. 25 depicts a perspective view of a docking prosthesis in accordance with another aspect of the disclosure, wherein the docking prosthesis is in its radially expanded configuration.
FIG. 26 is a perspective view of the docking prosthesis of FIG. 25 and a valve prosthesis disposed in the docking prosthesis, wherein the valve prosthesis further includes a plurality of skirt-reinforcement members in accordance with an aspect of the disclosure.

As mentioned above, the skirt-reinforcement members described herein may be applied to a docking prosthesis that is configured to receive a valve prosthesis therein. For example, FIG. 25 depicts a perspective view of a docking prosthesis 2500 in accordance with another aspect of the disclosure. The docking prosthesis 2500 includes a stent or frame 2502. The frame 2502 is tubular, with a plurality of side openings defined therein. In an embodiment, the plurality of side openings may be substantially diamond-shaped. The frame 2502 includes a skirt 2512 coupled to a surface thereof. More particularly, the skirt 2512 is coupled to an inner surface of the frame 2502 to line a portion thereof. Alternatively, the skirt 2512 may be coupled to an outer surface of the frame 2502 to enclose a portion thereof. The skirt 2512 may be formed from the same materials described above with respect to the inner skirt 112.

With reference to FIG. 26, the docking prosthesis 2500 is configured to receive a valve prosthesis 2600 therein. The valve prosthesis 2600 includes a frame 2602 and a prosthetic valve component 2608 including at least one leaflet 2609 disposed within and secured to the frame 2602. The prosthetic valve component 2608 of the valve prosthesis 2600 is capable of regulating flow therethrough via valve leaflets that may form a replacement valve. The prosthetic valve component 2608 may have three leaflets 2609, although a single leaflet or bicuspid leaflet configuration may alternatively be used in embodiments hereof. As described above with respect to the prosthetic valve component 108, when deployed in situ, the prosthetic valve component 2608 in a closed state is configured to block blood flow in one direction to regulate blood flow through a central lumen of the frame 2602. The valve leaflets 2609 may be attached to a skirt 2612, which is coupled to a surface of the frame 2602. More particularly, the skirt 2612 is coupled to an inner surface of the frame 2602 to line a portion thereof. Alternatively, the skirt 2612 may be coupled to an outer surface of the frame 2602 to enclose a portion thereof. The skirt 2612 may be formed from the same materials described above with respect to the inner skirt 112.

The skirt 2612 of the valve prosthesis 2600 may billow during opening and closing of the leaflets 2609 in situ, and the leaflets 2609 may contact the skirt 2612. Such billowing may undesirably result in contact between the skirt 2612 and the leaflets 2609 of the valve prosthesis 2600. If the leaflets 2609 contact the skirt 2612 during opening and closing, such contact may cause early leaflet tissue abrasion as well as early skirt abrasion. Additionally, the greater relative motion between the skirt 2612 and the frame 2602 may further induce early skirt abrasion. Thus, the valve prosthesis 2600 further includes a plurality of skirt-reinforcement members 2630. As described above with respect to the skirt-reinforcement members 730 described above, the skirt-reinforcement members 2630 reinforce the material of the skirt 2612 that spans across the side openings of the frame 2602 to limit the radial motion or billowing of the skirt material, thereby minimizing risk of damage to both the skirt 2612 and the leaflets 2609.

Each skirt-reinforcement member 2630 is a flexible tether that spans or extends between the skirt 2612 and the frame 2502 of the docking prosthesis 2500. Each skirt-reinforcement member 2630 may be formed from the same materials described above with respect to the skirt-reinforcement members 730. Each skirt-reinforcement member 2630 is configured to restrict or prevent billowing, or radial motion, of an unsupported portion of the skirt 2612 that spans across or extends over a side opening of the stent 2602. Each skirt-reinforcement member 2630 has a first end coupled to the frame 2502 of the docking prosthesis 2500 and a second end directly attached to the skirt 2612 along the unsupported portion of the skirt 2612 that spans one or more of the plurality of side openings of the stent 2602. Since the first end of the skirt-reinforcement member 2630 is coupled to the frame 2502 of the docking prosthesis 2500, the skirt-reinforcement member 2630 applies tension to the skirt 2612 and thereby prevents undesired billowing of the skirt material. The skirt-reinforcement member 2630 is configured to be under tension when the transcatheter valve prosthesis 2600 is in its radially expanded configuration, thereby mitigating movement of the skirt 2612 throughout the cardiac cycle.

The second end of the skirt-reinforcement member 2630 is directly attached to the inner skirt 2612 via any suitable attachment mechanism described herein with respect to the skirt-reinforcement members 730. In an embodiment, the first end of the skirt-reinforcement member 2630 is directly attached to the frame 2502 of the docking prosthesis 2500 via any suitable attachment mechanism described herein with respect to the skirt-reinforcement members 730. In another embodiment, the first end of the skirt-reinforcement member 2630 is directly attached to the outer skirt 2512 of the docking prosthesis 2500.

In the embodiment of FIG. 26, the plurality of skirt-reinforcement members 2630 are spaced apart from each other in approximately equal increments around the circumference of the stent 2602 and a skirt-reinforcement member 2630 is utilized only on the side openings having skirt material that may come into contact with leaflets 2609 when the leaflets are opening and closing in situ. At least one side opening must include a skirt-reinforcement member 2630 according to an aspect of the present disclosure.

Notably, the length of each skirt-reinforcement member 2630 is configured such that the skirt-reinforcement member 2630 is under tension when the valve prosthesis 2600 is in the radially expanded configuration. The skirt-reinforcement members are configured to have sufficient tension along its length when the valve prosthesis 2600 is in the expanded configuration to minimize radial movement of the skirt 2612 throughout the cardiac cycle. Further, in this embodiment, the docking prosthesis 2500 is delivered via the same delivery system (not shown) as the valve prosthesis 2600, so that the skirt-reinforcement member 2630 is pre-attached to each component.

Figure 27:
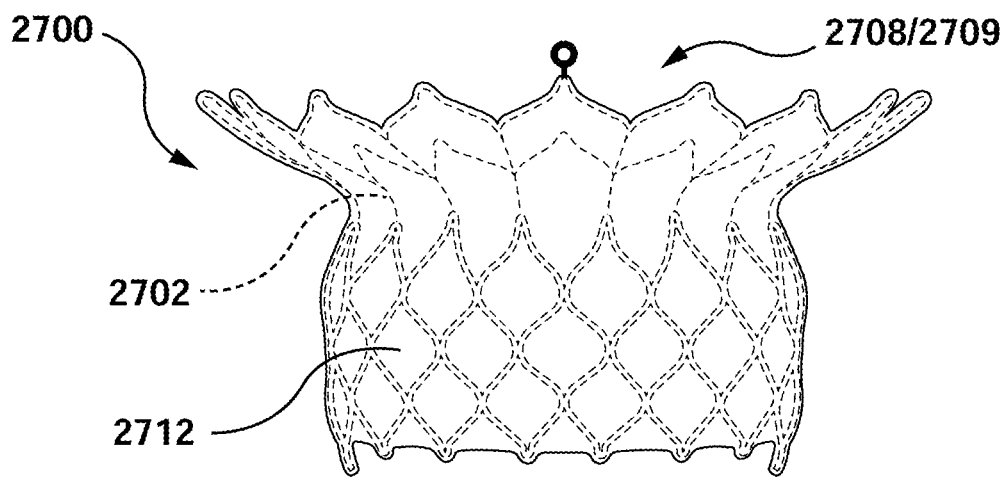
FIG. 27 depicts a perspective view of a valve prosthesis in accordance with another aspect of the disclosure, wherein the valve prosthesis is in its radially expanded configuration.
Figure 28:
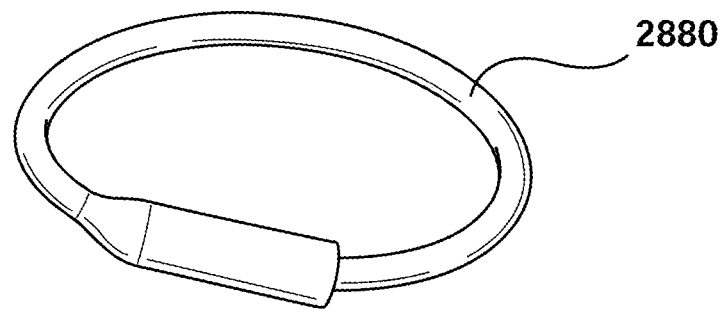
FIG. 28 is a perspective view of a docking component configured to receive the valve prosthesis of FIG. 27.
Figure 29:
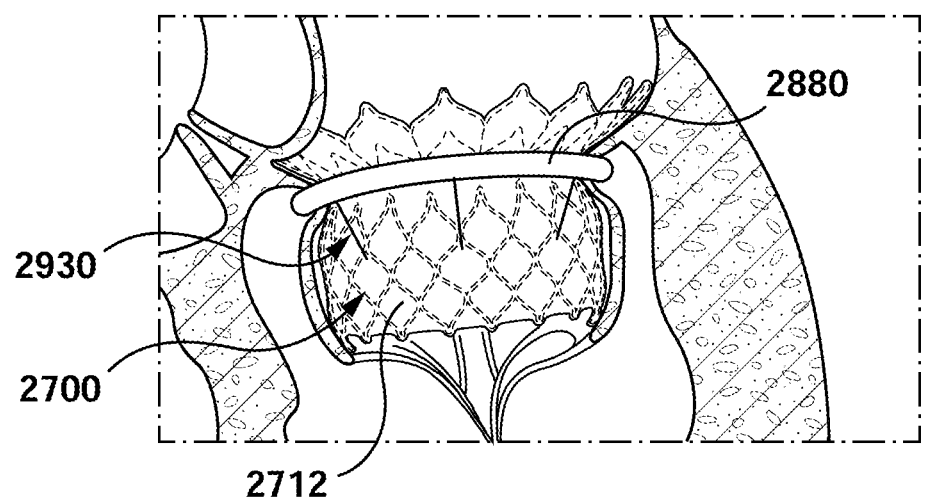
FIG. 29 is a perspective view of the docking component of FIG. 28 and the valve prosthesis of FIG. 27 disposed in the docking prosthesis in situ, wherein the valve prosthesis further includes a plurality of skirt-reinforcement members in accordance with an aspect of the disclosure.

FIGS. 27-29 illustrate another embodiment of skirt-reinforcement members applied to a docking component that is configured to receive a valve prosthesis therein. FIG. 27 illustrates a perspective view of a valve prosthesis 2700, FIG. 28 illustrates a perspective view of a docking component 2880 configured to receive the valve prosthesis 2700, and FIG. 29 illustrates the assembly of the docking component 2880 and the valve prosthesis 2700 received therein in situ within a native valve implantation site. In this embodiment, the docking component 2880 is an annular ring that is implanted within the native valve annulus prior to deployment of the valve prosthesis 2700. The docking component 2880 is further described in U.S. Pat. No. 9,358,108 to Bortlein et al. and/or U.S. Pat. No. 9,848,982 to Bortlein et al., each of which is herein incorporated by reference in its entirety. In another embodiment, the docking component may have a configuration as described in U.S. Pat. No. 10,463,479 to Manash et al.

With reference to FIG. 27, the valve prosthesis includes a frame 2702 and a prosthetic valve component 2708 including at least one leaflet 2709 disposed within and secured to the frame 2702. The prosthetic valve component 2708 of the valve prosthesis 2700 is capable of regulating flow therethrough via valve leaflets that may form a replacement valve. The prosthetic valve component 2708 may have three leaflets 2709, although a single leaflet or bicuspid leaflet configuration may alternatively be used in embodiments hereof. As described above with respect to the prosthetic valve component 108, when deployed in situ, the prosthetic valve component 2708 in a closed state is configured to block blood flow in one direction to regulate blood flow through a central lumen of the frame 2702. The valve leaflets 2709 may be attached to a skirt 2712, which is coupled to a surface of the frame 2702. More particularly, the skirt 2712 is coupled to an inner surface of the frame 2702 to line a portion thereof. Alternatively, the skirt 2712 may be coupled to an outer surface of the frame 2702 to enclose a portion thereof. The skirt 2712 may be formed from the same materials described above with respect to the inner skirt 112.

The skirt 2712 of the valve prosthesis 2700 may billow during opening and closing of the leaflets 2709 in situ, and the leaflets 2709 may contact the skirt 2712. Such billowing may undesirably result in contact between the skirt 2712 and the leaflets 2709 of the valve prosthesis 2700. If the leaflets 2709 contact the skirt 2712 during opening and closing, such contact may cause early leaflet tissue abrasion as well as early skirt abrasion. Additionally, the greater relative motion between the skirt 2712 and the frame 2702 may further induce early skirt abrasion. Thus, the valve prosthesis 2700 further includes a plurality of skirt-reinforcement members 2930. As described above with respect to the skirt-reinforcement members 730 described above, the skirt-reinforcement members 2930 reinforce the material of the skirt 2712 that spans across the side openings of the frame 2702 to limit the radial motion or billowing of the skirt material, thereby minimizing risk of damage to both the skirt 2712 and the leaflets 2709.

Each skirt-reinforcement member 2930 is a flexible tether that spans or extends between the skirt 2712 and the docking component 2880. Each skirt-reinforcement member 2930 may be formed from the same materials described above with respect to the skirt-reinforcement members 730. Each skirt-reinforcement member 2930 is configured to restrict or prevent billowing, or radial motion, of an unsupported portion of the skirt 2712 that spans across or extends over a side opening of the stent 2702. Each skirt-reinforcement member 2930 has a first end attached to the docking component 2880 and a second end directly attached to the skirt 2712 along the unsupported portion of the skirt 2712 that spans one or more of the plurality of side openings of the stent 2702. The first end of the skirt-reinforcement member 2930 is directly attached to the docking component 2880 via adhesive or welding. The second end of the skirt-reinforcement member 2930 is directly attached to the skirt 2712 via any suitable attachment mechanism described herein with respect to the skirt-reinforcement members 730. Since the first end of the skirt-reinforcement member 2930 is coupled to the docking component 2880, the skirt-reinforcement member 2930 applies tension to the skirt 2712 and thereby prevents undesired billowing of the skirt material. The skirt-reinforcement member 2930 is formed from a flexible material such that it is configured to slacken when the transcatheter valve prosthesis 2700 is in its radially compressed configuration, but is configured to be under tension when the transcatheter valve prosthesis 2700 is in its radially expanded configuration, thereby mitigating movement of the skirt 2712 throughout the cardiac cycle.

In the embodiment of FIG. 27, the plurality of skirt-reinforcement members 2930 are spaced apart from each other in approximately equal increments around the circumference of the stent 2702 and a skirt-reinforcement member 2930 is utilized only on the side openings having skirt material that may come into contact with leaflets 2709 when the leaflets are opening and closing in situ. At least one side opening must include a skirt-reinforcement member 2930 according to an aspect of the present disclosure.

Notably, the length of each skirt-reinforcement member 2930 is configured such that the skirt-reinforcement member 2930 is under tension when the transcatheter valve prosthesis 2700 is in the radially expanded configuration. The skirt-reinforcement members are configured to have sufficient tension along its length when the transcatheter valve prosthesis 2700 is in the expanded configuration to minimize radial movement of the skirt 2712 throughout the cardiac cycle. Further, in this embodiment, the docking component 2880 is delivered via the same delivery system (not shown) as the valve prosthesis 2700, so that the skirt-reinforcement member 2930 is pre-attached to each component.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A prosthesis having a radially expanded configuration and a radially compressed configuration, the prosthesis comprising:
   an inner frame including a plurality of crowns and a plurality of struts with each crown being formed between a pair of opposing struts, wherein a plurality of side openings is defined by the plurality of crowns and the plurality of struts;
   an outer frame coupled to and radially surrounding the inner frame;
   an inner skirt coupled to a surface of the inner frame, wherein the inner skirt extends over at least one side opening of the plurality of side openings of the inner frame; and
   a flexible tether that spans between the outer frame and the inner skirt, the flexible tether having a first end, a second end, and a length therebetween, wherein the first end of the flexible tether is coupled to the outer frame and the second end of the flexible tether is directly attached to the inner skirt along an unsupported portion of the inner skirt that spans the at least one side opening of the plurality of side openings of the inner frame.

2. The prosthesis of claim 1, wherein the flexible tether is an elongated strand of suture material.

3. The prosthesis of claim 1, wherein the length of the flexible tether is configured such that the flexible tether is under tension when the prosthesis is in the radially expanded configuration.

4. The prosthesis of claim 1, wherein the first end of the flexible tether is directly attached to the outer frame.

5. The prosthesis of claim 1, further comprising an outer skirt coupled to a surface of the outer frame, wherein the first end of the flexible tether is directly attached to the outer skirt.

6. The prosthesis of claim 1, wherein the flexible tether is one of a plurality of flexible tethers that are circumferentially spaced apart from each other.

7. The prosthesis of claim 1, wherein the prosthesis is a heart valve prosthesis and the prosthesis further comprises a prosthetic valve component disposed within and secured to the inner frame, the prosthetic valve being configured to block blood flow in one direction to regulate blood flow through a central lumen of the inner frame.

8. The prosthesis of claim 1, wherein each side opening of the at least one side opening has a width between 4% and 16% of a circumference of the inner frame.

9. The prosthesis of claim 1, wherein the flexible tether has a slackened configuration when the prosthesis is in the radially compressed configuration.

10. The prosthesis of claim 1, wherein the flexible tether is configured to prevent radial motion of the unsupported portion of the inner skirt when the prosthesis is in the radially expanded configuration.

11. The prosthesis of claim 1, wherein the inner frame includes a total of exactly nine side openings around a circumference of the inner frame.

12. The prosthesis of claim 1, wherein the flexible tether is one of a plurality of flexible tethers and each flexible tether of the plurality of flexible tethers is directly attached to skirt material of each side opening of the inner frame.

13. The prosthesis of claim 1, wherein the prosthesis is a heart valve prosthesis and the prosthesis further comprises a prosthetic valve component having a plurality of leaflets disposed within and secured to the inner frame, the prosthetic valve being configured to block blood flow in one direction to regulate blood flow through a central lumen of the inner frame, and wherein the flexible tether is one of a plurality of flexible tethers and a flexible tether is attached only to skirt material of side openings which is likely to come into contact with a leaflet of the plurality of leaflets when the leaflets are opening and closing in situ.

14. The prosthesis of claim 13, wherein the prosthesis includes a total of three flexible tethers that are spaced apart from each other in approximately equal increments around a circumference of the inner frame.

15. A prosthesis having a radially expanded configuration and a radially compressed configuration, the prosthesis comprising:
an inner frame including a plurality of crowns and a plurality of struts with each crown being formed between a pair of opposing struts, wherein a plurality of side openings is defined by the plurality of crowns and the plurality of struts;
an outer frame coupled to and radially surrounding the inner frame;
an inner skirt coupled to a surface of the inner frame, wherein the inner skirt extends over at least one side opening of the plurality of side openings of the inner frame;
a prosthetic valve component having a plurality of leaflets disposed within and secured to the inner frame, the prosthetic valve being configured to block blood flow in one direction to regulate blood flow through a central lumen of the inner frame,
a plurality of flexible tethers, wherein each flexible tether spans between the outer frame and the inner skirt, each flexible tether having a first end, a second end, and a length therebetween, wherein the first end of each flexible tether is coupled to the outer frame and the second end of each flexible tether is directly attached to the inner skirt along an unsupported portion of the inner skirt that spans the at least one side opening of the plurality of side openings of the inner frame; and
wherein a flexible tether of the plurality of flexible tethers is attached only to skirt material of side openings which is likely to come into contact with a leaflet of the plurality of leaflets when the leaflets are opening and closing in situ.

16. The prosthesis of claim 15, wherein the prosthesis includes a total of three flexible tethers that are spaced apart from each other in approximately equal increments around a circumference of the inner frame.

17. The prosthesis of claim 15, wherein each flexible tether is an elongated strand of suture material.

18. The prosthesis of claim 15, wherein each flexible tether has a slackened configuration when the prosthesis is in the radially compressed configuration and the length of the flexible tether is configured such that the flexible tether is under tension when the prosthesis is in the radially expanded configuration.

19. The prosthesis of claim 15, wherein each side opening of the at least one side opening has a width between 4% and 16% of a circumference of the inner frame.

20. The prosthesis of claim 15, wherein the flexible tether is configured to prevent radial motion of the unsupported portion of the inner skirt when the prosthesis is in the radially expanded configuration.

* * * * *